(12) United States Patent
Kowall et al.

(10) Patent No.: US 12,426,894 B2
(45) Date of Patent: Sep. 30, 2025

(54) SURGICAL SAW BLADE CARTRIDGE AND COUPLER THEREFOR

(71) Applicant: Stryker Corporation, Kalamazoo, MI (US)

(72) Inventors: Wyatt S. Kowall, Portage, MI (US); Jeffrey Karl, Kalamazoo, MI (US); Girish Karve, Portage, MI (US); Steven J. Carusillo, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 191 days.

(21) Appl. No.: 18/004,234

(22) PCT Filed: Jul. 23, 2021

(86) PCT No.: PCT/US2021/042898
§ 371 (c)(1),
(2) Date: Jan. 4, 2023

(87) PCT Pub. No.: WO2022/020678
PCT Pub. Date: Jan. 27, 2022

(65) Prior Publication Data
US 2023/0263534 A1    Aug. 24, 2023

Related U.S. Application Data

(60) Provisional application No. 63/055,585, filed on Jul. 23, 2020.

(51) Int. Cl.
*A61B 17/14* (2006.01)
*A61B 17/00* (2006.01)

(52) U.S. Cl.
CPC .. *A61B 17/142* (2016.11); *A61B 2017/00477* (2013.01)

(58) Field of Classification Search
CPC ........ A61B 17/142; A61B 2017/00477; A61B 17/162
See application file for complete search history.

(56) References Cited

U.S. PATENT DOCUMENTS 7,691,106 B2 *  4/2010  Schenberger ........ A61B 17/142
                                                 606/82
7,833,741 B2    11/2010  Ciceri et al.
(Continued)

FOREIGN PATENT DOCUMENTS

EP        0776634 A2     6/1997
WO    2004043269 A1     5/2004
(Continued)

OTHER PUBLICATIONS

Partial International Search Report for Application No. PCT/US2021/042898 dated Oct. 14, 2021, 2 pages.
(Continued)

*Primary Examiner* — Julian W Woo
(74) *Attorney, Agent, or Firm* — Howard & Howard Attorneys PLLC

(57) ABSTRACT

A saw blade cartridge comprises a saw blade and a cassette. The cassette is disposed over a proximal portion of the saw blade and includes first and second cassette portions opposing each other across the proximal portion. Each portion comprises a shell and a damper. The shells are of a first stiffness and have an outer side. The dampers are of a second stiffness less than the first stiffness and are disposed on an inner side of the shell. The cassette portions are substantially fixed relative to the proximal portion and are substantially aligned with each other. The shells are fixed to each other. The dampers contact the proximal portion. A handpiece coupler for engaging either of the saw blade cartridge or a
(Continued)

saw blade includes a release button with a lock button slidably disposed therein to resist unintended opening.

18 Claims, 22 Drawing Sheets

(56) References Cited

U.S. PATENT DOCUMENTS

| | | | |
|---|---|---|---|
| 9,402,635 | B2 | 8/2016 | Boykin et al. |
| 11,364,036 | B2 * | 6/2022 | Hassler, Jr. ............ A61B 17/15 |
| 2009/0312762 | A1 | 12/2009 | Boykin |
| 2013/0204256 | A1 | 8/2013 | Wang et al. |
| 2016/0016239 | A1 * | 1/2016 | DeSoutter ............ A61B 17/142 |
| | | | 403/373 |

FOREIGN PATENT DOCUMENTS

| | | |
|---|---|---|
| WO | 2014135868 A1 | 9/2014 |
| WO | 2017106533 A2 | 6/2017 |

OTHER PUBLICATIONS

International Search Report for Application No. PCT/US2021/042898 dated Dec. 23, 2021, 2 pages.

* cited by examiner

SURGICAL SAW BLADE CARTRIDGE AND COUPLER THEREFOR

CROSS-REFERENCE TO RELATED APPLICATIONS

The present application is a National Stage of International Patent Application No. PCT/US2021/042898, filed on Jul. 23, 2021, which claims priority to and all the benefits of U.S. Provisional Patent Application No. 63/055,585 filed on Jul. 23, 2020, each of which is hereby expressly incorporated herein by reference in its entirety.

BACKGROUND

A saw blade, for example, a sagittal saw blade, may oscillate at its distal end, in a direction normal to a planar blade surface. Such oscillation has been labeled "blade whip." A saw blade cartridge that reduces blade whip is desired.

DETAILED DESCRIPTION

Figure 1:
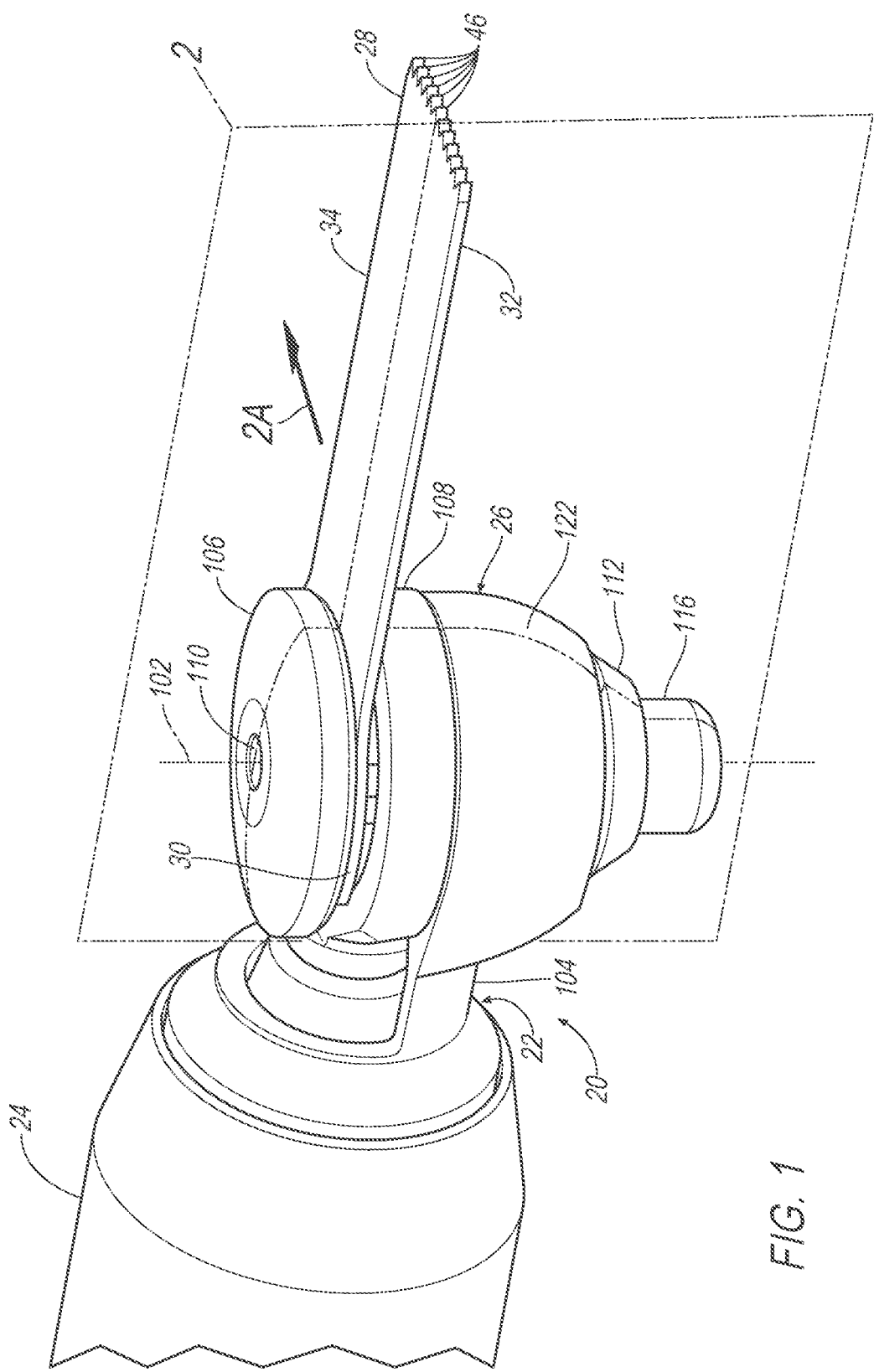
FIG. 1 is a perspective view of a distal portion of an example handpiece including an example coupler in receipt of an example sagittal saw blade.

The prior art does not address the need to provide one of either a saw blade or a saw blade cartridge that reduces blade whip.

A saw blade cartridge, for use with a powered surgical saw, comprises a saw blade and a cassette. The saw blade includes a proximal portion, a distal portion and a blade body. The proximal portion includes a driving surface and a mount axis. The distal portion includes cutting teeth. The blade body is between the distal and proximal portions. The cassette is disposed over the proximal portion and includes first and second cassette portions. The cassette portions are opposed across the proximal portion. Each cassette portion comprises a shell and a damper. Each shell is of a first material and has a substantially planar outer side and an opposed inner side with an associated inner edge. Each damper is of a second material against an inner side of the shell. The damper extends beyond the inner edge of the shell. The cassette portions are in substantial alignment with each other and are substantially fixed relative to the proximal portion. The shells are fixed to each other with the dampers contacting the proximal portion. A stiffness of the shells is greater than a stiffness of the dampers.

The saw blade cartridge and the features thereof may comprise additional features and modifications as set forth below, such features and modifications being included separately or in combination with each other, with such combinations being limited only by mutual exclusivity.

The first stiffness may be greater than the second stiffness.

The dampers may apply a predetermined clamp load to the proximal portion.

The cassette portions may be substantially identical.

The shells may be formed of a first material and the dampers may be formed of a second material.

The second material may be elastomeric.

The inner side of each shell may define a receiving pocket for the respective damper. Each pocket may be in receipt of the corresponding damper.

Each damper may extend beyond the inner edge of the respective shell.

The shells may have a substantially arcuate shape centered on the mount axis.

The driving surface may be defined by at least one of a notch and an aperture.

The cassette does not entirely overlap all of the driving surface.

The proximal portion of the saw blade may have a first thickness, and may be substantially planar. Also, the blade body may be substantially planar and may have a second thickness.

The outer sides of the first and second cassette portion may be substantially planar and the cartridge may have a substantially uniform third thickness across the outer sides.

The shell of at least one of the first and second cassette portions may include a connecting tab extending beyond the associated inner edge.

The connecting tab may be disposed in a connecting opening in the saw blade.

The connecting tab may be fixed to the shell of the shell of the opposed cassette portion.

The dampers may be axially compressed against the proximal portion of the saw blade by the shells.

The dampers may each define a continuous arc of at least 120 degrees.

A handpiece coupler, for engaging either of a surgical saw blade and a surgical saw blade cartridge, comprises a housing head, a driver, a cup, a pin, a cap, a release button, a coupler spring and a lock button. The housing head defines a pivot bore centered on an axis. The driver is axially fixed to the housing head and is pivotable about the axis. The driver defines a driver bore passing therethrough, with the bore substantially centered on the axis. The driver includes a blade engagement prong on a first side of the driver that is radially spaced from the axis. The cup is fixed to the driver for unitary movement therewith. The cup has an inside wall surface substantially centered on the axis. The cup axially extends from a second side of the driver into the pivot bore. The pin is slidably disposed in the driver bore and the cup for selective axial displacement therein and relative thereto. The cap is fixed to a first end of the pin. The cap extends radially beyond the prong. The release button is fixed to a second end of the pin for selective engagement by a user. The release button defines a lock cavity therein. The lock cavity and an outer surface of the release button define a button wall therebetween. The coupler spring is disposed between the driver and the pin biasing the pin toward a closed position. The lock button is slidably disposed in the lock cavity and has two locked positions and an unlocked position therein.

The coupler and the components and features thereof may comprise additional features and modifications as set forth below, such features and modifications being included separately or in combination with each other, with such combinations being limited only by mutual exclusivity.

The lock button may comprise part of a position lock, the position lock further comprising a lock spring disposed between the lock button and the pin and the lock spring biasing the lock button toward the locked position.

The position lock may further comprise a first slider and a second slider. The release button may have formed therein an open first end of the cavity, a first slider aperture, and a second slider aperture. The first slider aperture may be in slidable receipt of the first slider. The first slider aperture may pass through the button wall at a first axial and circumferential location. The second slider aperture may be in slidable receipt of the second slider. The second slider aperture may pass through the button wall in a second axial location offset from the first axial location and a second circumferential location offset from the first circumferential location.

The lock button may extend beyond a first end of the button wall in the locked position and may be substantially flush with the first end of the button wall in the unlocked position.

The position lock may further comprise a plurality of notches in the inside wall surface of the cup and an outer surface of the lock button for selective engagement by the sliders.

The plurality of notches may include a first lock button receiving notch, a first cup receiving notch, a second cup receiving notch, and a second lock button receiving notch. The first lock button receiving notch may be in the outer surface of the lock button. The first cup receiving notch may be in the inside wall surface of the cup. The second cup receiving notch may be in the inside wall surface of the cup. The second lock button receiving notch may be in the outer surface of the lock button.

The first slider may be disposed at least in part in the first slider aperture for axial movement with the release button in all positions of the release button and the lock button. The first slider may also be disposed in part in the first cup receiving notch with the release button in a first retaining position and the lock button in a first locked position. The first slider may also be disposed in part in the first lock button receiving notch with the release button in the first retaining position through a first release position and the lock button in the unlocked position. The first slider may also be disposed in part in the first lock button receiving notch with the release button in a second retaining position and the lock button in a second locked position. The first slider may also be disposed in part in the first lock button receiving notch with the release button in the second retaining position through a second release position and the lock button in the unlocked position. The second slider may be disposed at least in part in the second slider aperture for axial movement with the release button in all positions of the release button and the lock button. The second slider may also be disposed in part in the second cup receiving notch with the release button in the first retaining position and the lock button in the first locked position. The second slider may also be disposed in part in the second lock button receiving notch with the release button in the first retaining position through the first release position of the release button and the lock button in the unlocked position. The second slider may also be disposed in part in the second cup receiving notch with the release button in the second retaining position and the lock button in the second locked position. The second slider may also be disposed in part in the second lock button receiving notch with the release button in the second retaining position through the second release position of the release button and the lock button in the unlocked position.

The first retaining position may be achieved when a blade without a damper cassette is received by the coupler. The second retaining position may be achieved when a blade cartridge including the damper cassette is received by the coupler.

The lock button may comprise part of the position lock which may further comprise a twin first slider and a twin second slider. The release button may have formed therein a twin first slider aperture and a twin second slider aperture. The twin first slider aperture may be in slidable receipt of the twin first slider and may pass through the button wall. The twin second slider aperture may be in slidable receipt of the twin second slider and may pass through the button wall.

The position lock further comprises a plurality of notches in the inside wall surface of the cup and an outer surface of the lock button for selective engagement by the sliders.

The plurality of notches may include a first lock button receiving notch, a mirror image first lock button receiving notch, a first cup receiving notch, a mirror image first cup receiving notch, a second cup receiving notch, a mirror image second cup receiving notch, a second lock button receiving notch, and a mirror image second lock button receiving notch. The first lock button receiving notch and the mirror image first lock button receiving notch may be in the outer surface of the lock button. The first cup receiving notch and the mirror image first cup receiving notch may be in the inside wall surface of the cup. The second cup receiving notch and the mirror image second cup receiving notch may be in the inside wall surface of the cup, The second lock button receiving notch and the mirror image second lock button receiving notch may be in the outer surface of the lock button.

The first slider may be disposed at least in part in the first slider aperture for axial movement with the release button in all positions of the release button and the lock button. The first slider may also be disposed in part in the first cup receiving notch with the release button in a first retaining position and the lock button in a first locked position. The first slider may also be disposed in part in the first lock button receiving notch with the release button in the first retaining position through a first release position and the lock button in the unlocked position. The first slider may also be disposed in part in the first lock button receiving notch with the release button in a second retaining position and the lock button in a second locked position. The first slider may also be disposed in part in the first lock button receiving notch with the release button in the second retaining position through a second release position and the lock button in the unlocked position. The first twin slider may be disposed at least in part in the twin first slider aperture for axial movement with the release button in all positions of the release button and the lock button. The first twin slider may also be disposed in part in the mirror image first cup receiving notch with the release button in a first retaining position and the lock button in the first locked position. The first twin slider may also be disposed in part in the mirror image first lock button receiving notch with the release button in the first retaining position through a first release position and the lock button in the unlocked position. The first twin slider may also be disposed in part in the mirror image first lock button receiving notch with the release button in a second retaining position and the lock button in the second locked position. The first twin slider may also be disposed in part in the mirror image first lock button receiving notch with the release button in the second retaining position through a second release position and the lock button in the unlocked position. The second slider may be disposed at least in part in the second slider aperture for axial movement with the release button in all positions of the release button and the lock button. The second slider may also be disposed in part in the second cup receiving notch with the release button in the first retaining position and the lock button in the first locked position. The second slider may also be disposed in part in the second lock button receiving notch with the release button in the first retaining position through the first release position of the release button and the lock button in the unlocked position. The second slider may also be disposed in part in the second cup receiving notch with the release button in the second retaining position and the lock button in the second locked position. The second slider may also be disposed in part in the second lock button receiving notch with the release button in the second retaining position through the second release position of the release button and the lock button in the unlocked position. The twin second slider may be disposed at least in part in the twin second slider aperture for axial movement with the release button in all positions of the release button and the lock button. The twin second slider may also be disposed in part in the mirror image second cup receiving notch with the release button in the first retaining position and the lock button in the first locked position. The twin second slider may also be disposed in part in the mirror image second lock button receiving notch with the release button in the first retaining position through the first release position of the release button and the lock button in the unlocked position. The twin second slider may also be disposed in part in the mirror image second cup receiving notch with the release button in the second retaining position and the lock button in the second locked position. The twin second slider may also be disposed in part in the mirror image second lock button receiving notch with the release button in the second retaining position through the second release position of the release button and the lock button in the unlocked position.

The first retaining position may be achieved when a blade without a damper cassette is received by the coupler. The second retaining position may be achieved when a blade cartridge including the damper cassette is received by the coupler.

The sliders may be substantially rigid spheres.

Relative orientations and directions (by way of example, distal, proximal, upper, lower, bottom, rearward, front, rear, back, outboard, inboard, inward, outward, lateral, left, right) are set forth in this description not as limitations, but for the convenience of the reader in picturing at least one embodiment of the structures described. Such exemplary orientations may be from the perspective of a user of a saw.

The elements shown may take many different forms and may include multiple and/or alternate components and facilities. The example components illustrated are not intended to be limiting. Indeed, additional or alternative components and/or implementations may be used. Further, the elements shown are not necessarily drawn to scale unless explicitly stated as such.

Disclosed herein are a blade cartridge and couplers for accommodating a plurality of blade thicknesses.

As illustrated in FIGS. 1-4, a saw system 20, a form of a surgical tissue cutting system, includes a powered surgical saw 22 having a handpiece 24 with a first example coupler 26 for retention of both saw blades and saw blade cartridges. The handpiece 24 may be of the type used as an oscillating saw, including the type used to drive sagittal saw blades and sagittal saw blade cartridges. The handpiece 24 may have an example oscillation displacement range of five to eight degrees. An example commercially available powered surgical handpiece may be provided by a RemB™ Sagittal Saw handpiece by Stryker. The operation of such handpieces is well known. The coupler 26 of the system may be used to retain saw blades and saw blade cartridges respectively having a proximal portion of one of a first thickness and a second thickness, where the second thickness may be at least four times thicker than the first thickness. A prior-art coupler, suitable for engaging blades alone, is illustrated and described in U.S. Pat. No. 7,833,241 B2, assigned to Stryker Corporation.

Figure 3:
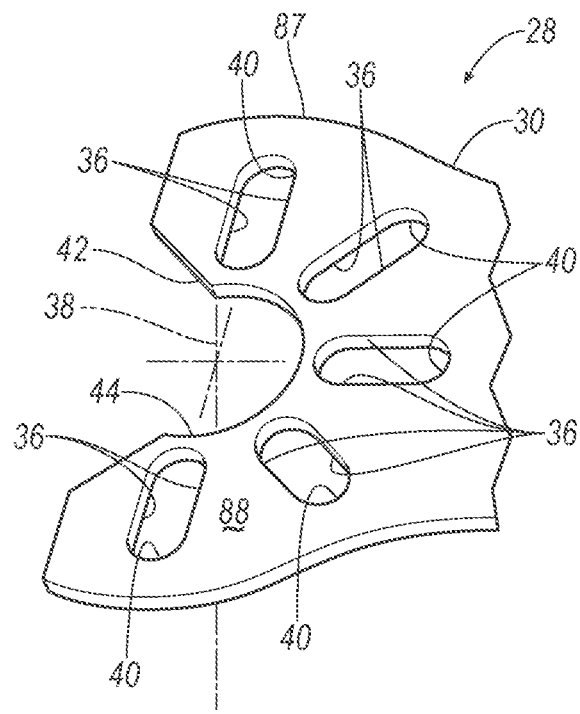
FIG. 3 is a perspective view of an example proximal portion of the example blade of FIG. 1.

An example sagittal saw blade 28, or more concisely, a saw blade 28, includes a proximal portion 30, a distal portion 32, and a blade body 34 disposed between the proximal portion 30 and the distal portion 32. The blade body 34 connects the proximal portion 30 and the distal portion 32. The proximal portion 30 as best shown in FIG. 3 includes a driving surface 36 and a mount axis 38. The proximal portion may more specifically include a plurality of blade apertures 40 defining a plurality of driving surfaces 36. The proximal portion 30 may also include a receiving slot 42 having a locating radial surface 44 at an end of the receiving slot 42. The distal portion 32 includes cutting teeth 46. Blades such as the blade 28 are known.

Figure 5:
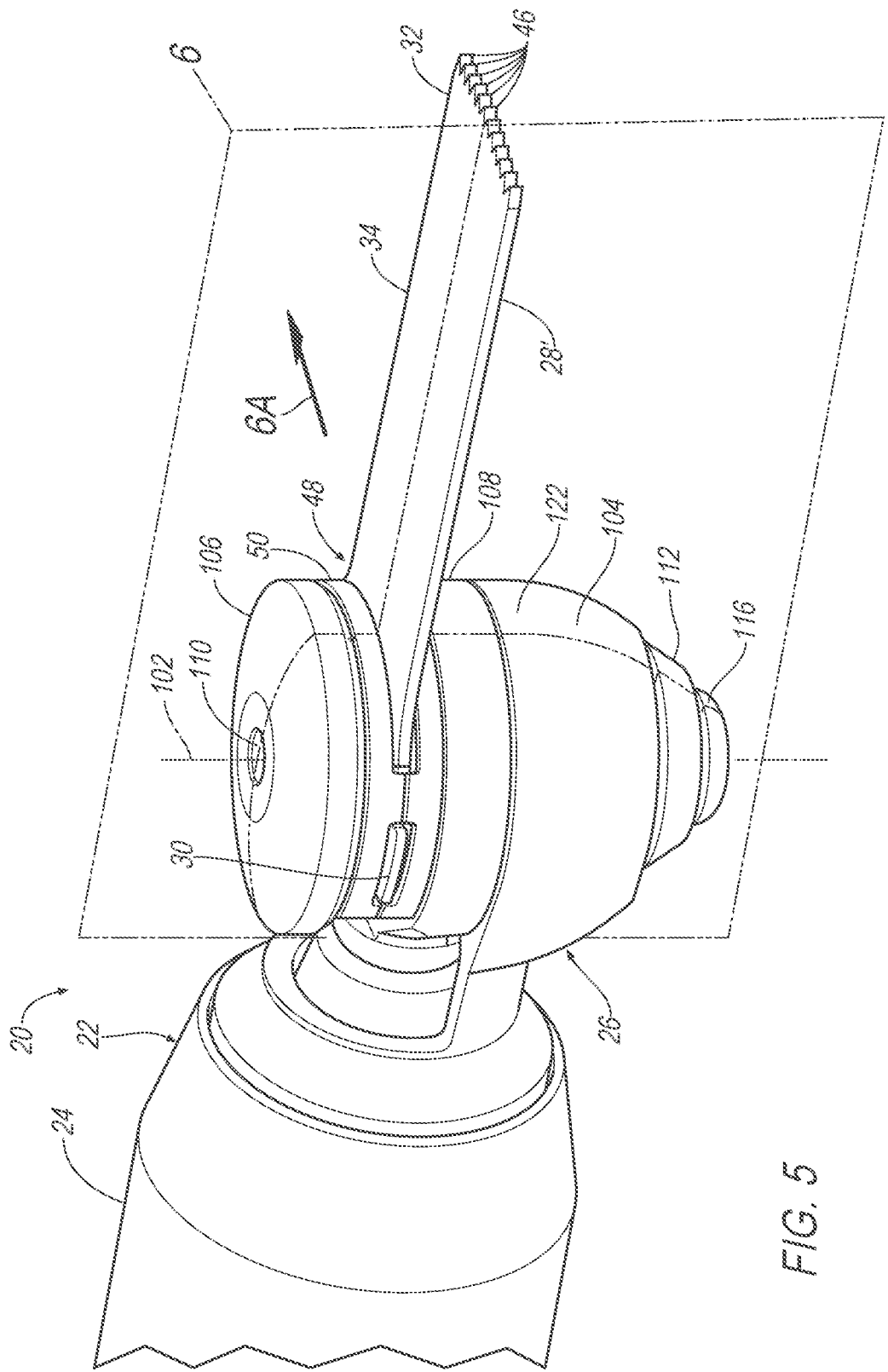
FIG. 5 is perspective view of a distal portion of the example handpiece and coupler of FIG. 1 in receipt of an example sagittal saw blade cartridge.
Figure 6:
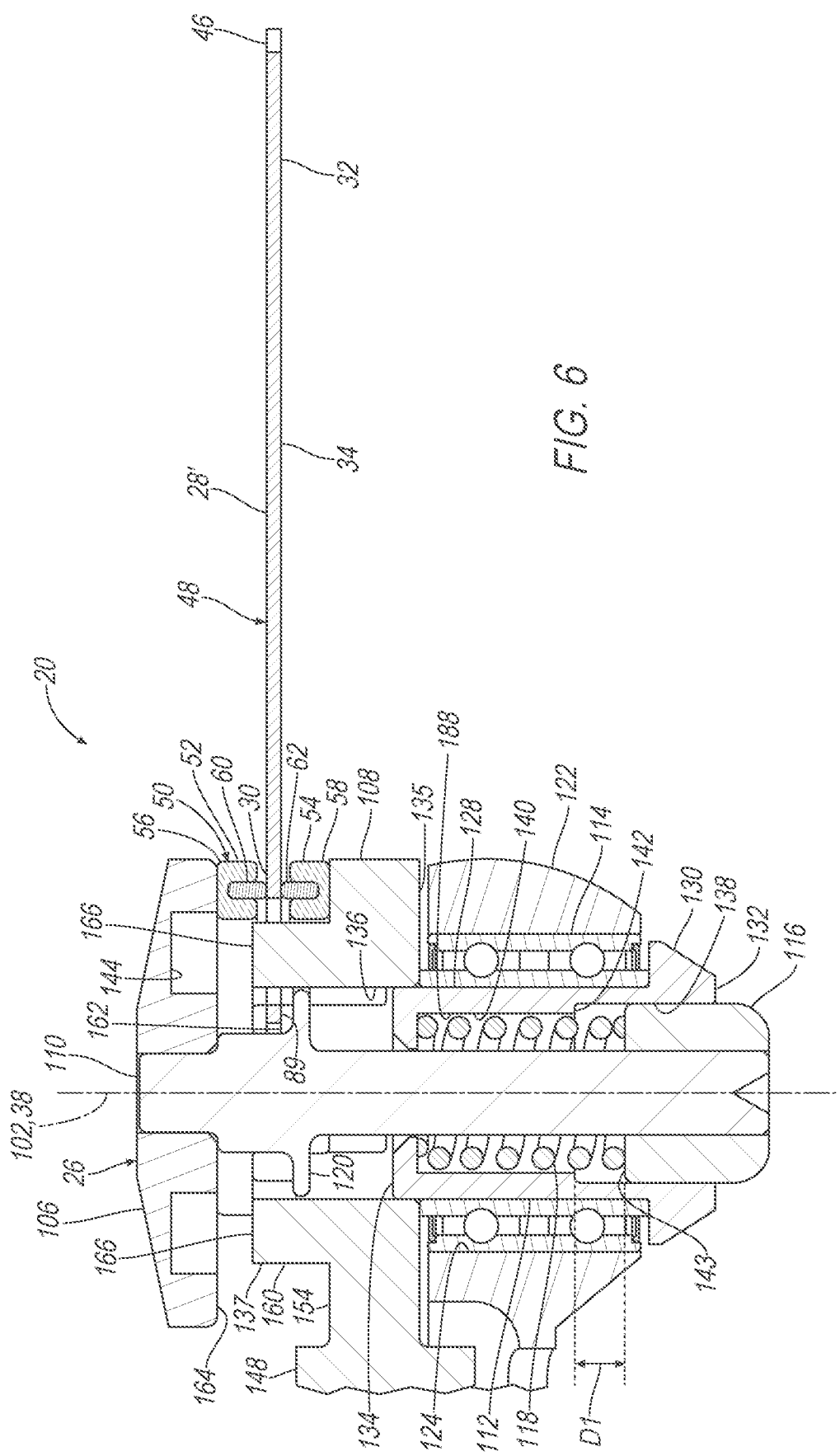
FIG. 6 is a sectional side view of the example coupler and blade cartridge of FIG. 5 through plane 6 in the direction of arrows 6A.
Figure 7:
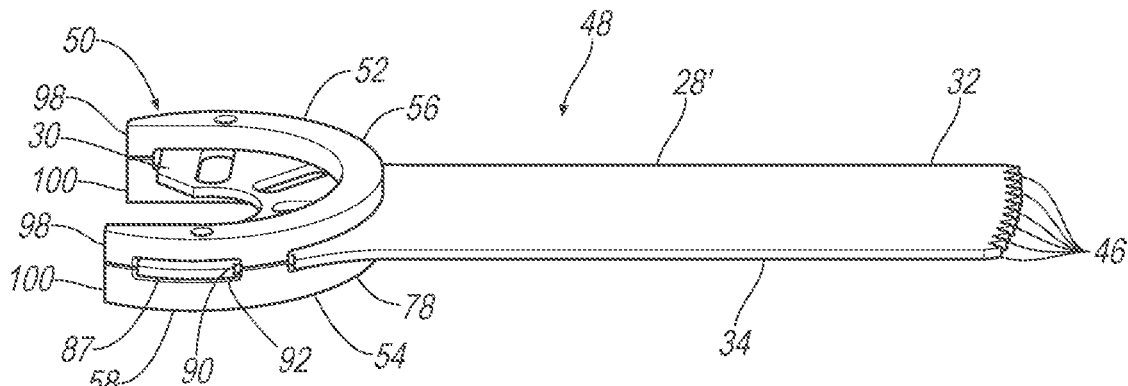
FIG. 7 is a perspective view of the example blade cartridge of FIG. 5 and FIG. 6.

As illustrated in FIGS. 5-11, the saw system 20 may include the powered surgical saw 22 with the handpiece 24, and an example sagittal saw blade cartridge 48, or more concisely, a saw blade cartridge 48. The saw blade cartridge 48 may be selectively removably mounted in the example handpiece 24 as illustrated in FIG. 5 and FIG. 6.

Figure 10:
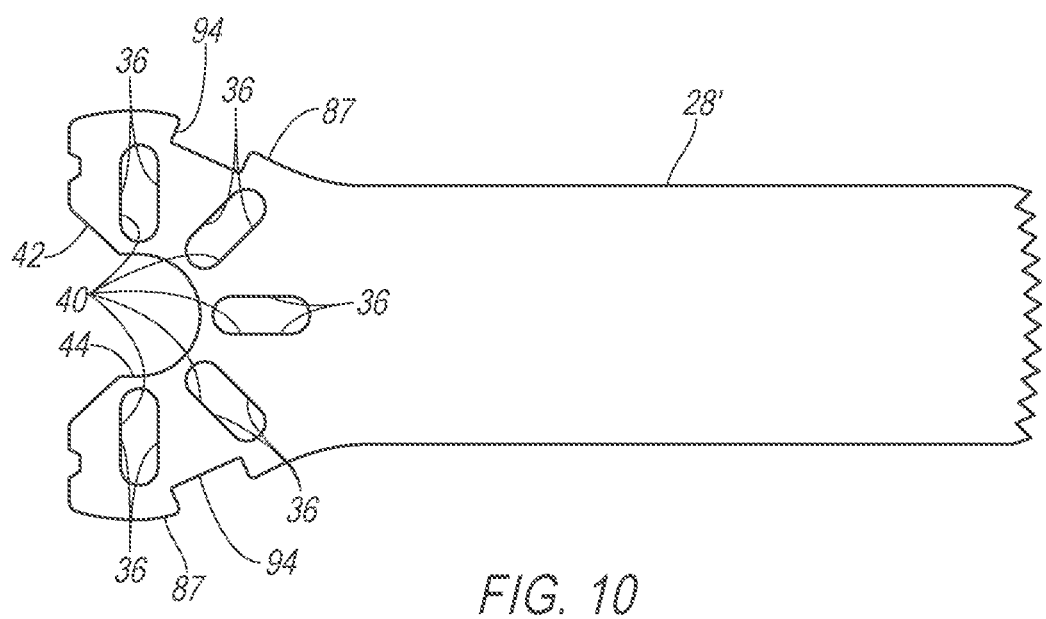
FIG. 10 is a top view of an example saw blade of the cartridge of FIGS. 5-9.
Figure 11:
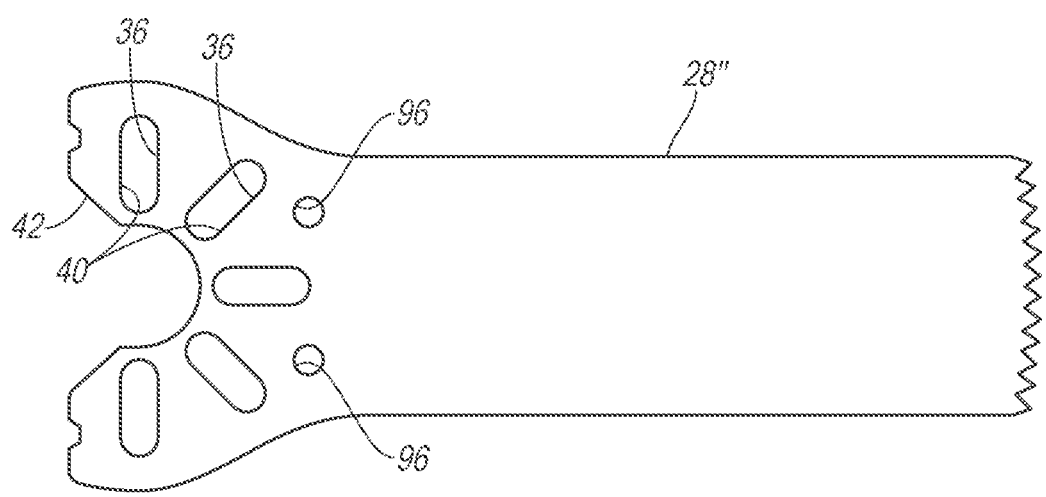
FIG. 11 is a top view of an example saw blade, such being an alternative to the saw blade of FIG. 10.

The saw blade cartridge 48 may include a saw blade 28', as illustrated in FIG. 10, much like the above-described saw blade 28, together with a damper cassette 50 also referenced to herein as a cassette 50. The saw blade 28', consistent with the above, includes a proximal portion 30', a distal portion 32, and a blade body 34 between the distal and proximal portions 32, 30'. The distal portion 32 includes the cutting teeth 46. The proximal portion 30' includes at least one driving surface 36 and the mount axis 38. The driving surface 36 is defined by at least one of a notch and the aperture 40. An example notch could be formed by extending the illustrated aperture 40 through a peripheral edge of the proximal portion 30'.

The cassette 50 comprises a first cassette portion 52 and a substantially identical second cassette portion 54. The first and second cassette portions 52, 54 may oppose each other across the proximal portion 30' of the blade 28'. The cassette portions 52, 54 are in substantial alignment with each other and are substantially fixed to each other and relative to the proximal portion 30' of the blade 28'. Each cassette portion 52, 54 includes a shell 56 and 58 respectively, and a damper 60 and 62 respectively. More specifically, the first cassette portion 52 includes a first shell 56 and a first damper 60, and the second cassette portion 54 includes a second shell 58 and a second damper 62.

The shells 56, 58 are formed of a first material having a first resistance to deflection in a clamping direction, alternatively stated, a first stiffness, and the dampers 60, 62 may be formed of a second material having a second resistance to deflection in a clamping direction, alternatively stated, a second stiffness, less than the first stiffness. An example first material may be by way of example and not limitation, a thermoset plastic or a thermoplastic or a metal such as stainless steel. An example durometer rating for the shell material, e.g., a substantially rigid plastic, may be a Shore D hardness of 50 or above. An example second material, alternatively referenced to herein as, a damper material, may be by way of example and not limitation any of a thermoset plastic or a thermoplastic or a silicone polymer or a nitrile rubber. An example durometer rating for the damper material may be a Shore A hardness of 50 or less.

A variety of hardness values can be feasibly used to reduce vibration transmission to the blade 28. In general, dampers 60, 62 of lower hardness will result in greater vibration attenuation by reducing damper stiffness. An alternative method to improve vibration attenuation is to either decrease the contact area between the blade 28 and the damper 60, 62, or increase the total height of the damper 60, 62. Altering both of these parameters will alter the effective stiffness of the damper 60, 62. Additionally, the magnitude of vibration attenuation is believed to also be dependent on the size of the blade 28, in that smaller blades 28 require reduced damper 60, 62 stiffness to achieve similar magnitudes of vibration attenuation that would be observed if a larger blade were to be used. Additionally, decreases damper stiffness too low may result in undesirable reduced rigidity of the blade 28 in the coupler 26 to mount the blade to the handpiece 24. For these reasons, it is believed that there is an ideal damper hardness as a function of blade size and density, blade 28 to damper contact area, damper height, and user preference. An estimated material hardness for the blade 28 shown in the figures may be a Shore 00 hardness of 20.

The shells 56, 58 each have a substantially planar outer side 64, 66 and an opposed inner side 68, 70 with an associated inner edge 72, 74. The inner edge 72, 74 may be on an outer periphery 76, 78 of the associated shell 56, 58. The shells 56, 58 may each have a substantially arcuate shape. When installed on the saw blade 28', the arcuate shape of the shells 56, 58 may be centered on the mount axis 38. The inner sides 68, 70 may each define a receiving pocket 80, 82 for receipt of their respective dampers 60, 62. Alternatively, each inner side 68, 70, may define a plurality of such pockets 80, 82, with each pocket 80, 82 in receipt of a separate damper 60, 62.

The dampers 60, 62 may be fixed to the shells 56, 58 by an adhesive or by being molded therein, or by any other known means. Injecting apertures 84 may be provided in the shells 56, 58 to accommodate molding of the dampers 60, 62 therein by injection of the damper material through the injecting apertures 84 into a mold defined in part by the shells 56, 58. The dampers 60, 62 extend in an axial direction beyond the inner edges 72, 74.

Figure 8:
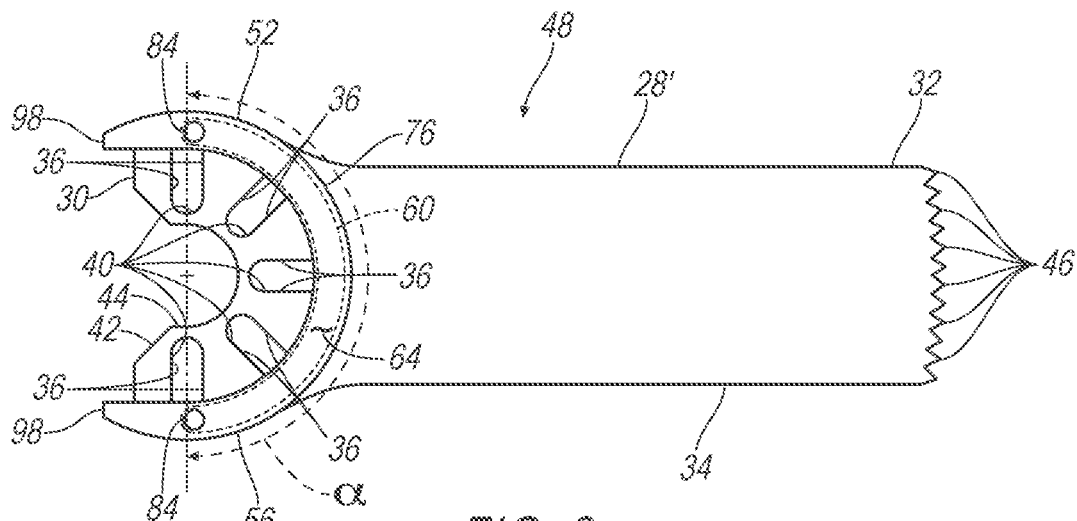
FIG. 8 is a top view of the example blade cartridge of FIG. 7.
Figure 9:
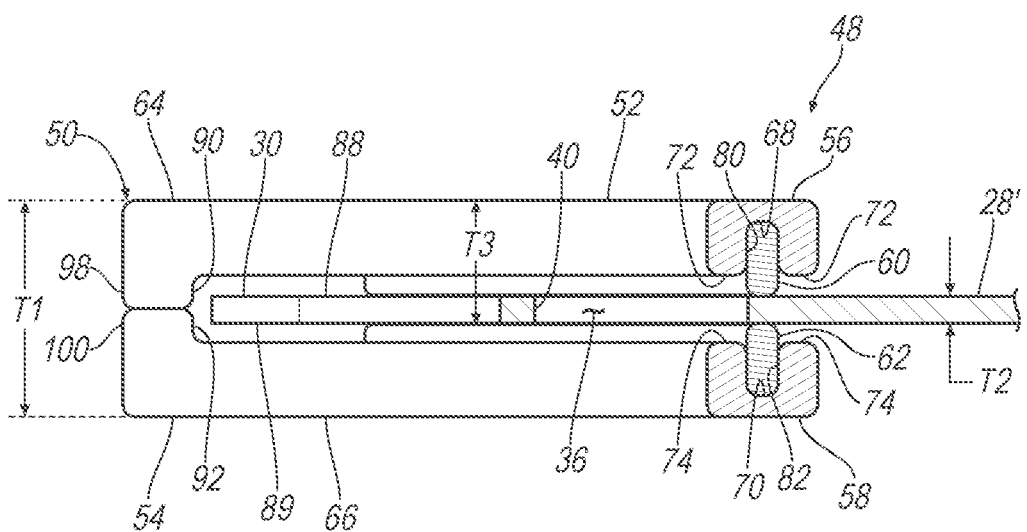
FIG. 9 is a sectional side view of the example blade cartridge of FIG. 7.

The shells 56, 58, and thus the cassette portions 52, 54, may have at least a portion of their respective outer peripheries 76, 78 substantially aligned with an outer peripheral edge 87 of the proximal portion 30' of the saw blade 28'. Inner peripheries of the cassette portions 52, 54 and thus the cassette 50 are substantially clear of the driving surfaces 36. However, there may be some overlap of the driving surfaces 36 by the cassette 50, so long as the cassette 50 does not overlap the driving surfaces 36 entirely and so long as there is no interference with the receipt of the saw blade cartridge 48 by the coupler 26. A cassette thickness T1 measured across the outer sides 64, 66 of the first and second cassette portions 52, 54 is substantially thicker than a blade thickness T2 of the blade 28'. An example blade thickness T2 may be 0.5 mm, and may be measured across a top surface 88 and a bottom surface 89 of the proximal portion 30' of the blade 28'. An example cassette thickness T1 may be 3.0 mm. The shells 56, 58 and the dampers 60, 62 may each define an arc α of at least 120 degrees. The arc α as illustrated in FIG. 8 is substantially equal to 180 degrees.

At least one of the cassette portions 52, 54 may be provided with a connecting tab 90, 92, respectively, extending axially beyond the associated inner edge 72, 74. When the cassette portions 52, 54 are installed on the blade 28', the connecting tab 90, 92 of the at least one of the cassette portions 52, 54 extends beyond the associated inner edge 72, 74 to connect with the opposing cassette portion 54, 52. Such connection may be by way of the connecting tab 90, 92 extending into a connecting opening, for example a connecting recess 94, on the outer peripheral edge 87 of the blade 28' as shown in FIG. 10. With an alternatively configured saw blade 28", illustrated in FIG. 11, a proximal portion 30" may have connecting apertures 96 as an alternative openings to the connecting recesses 94. In such an example, the tabs 90, 92 would be located so as to align with the apertures 96. A plurality of tabs may be provided on each of the cassette portions. When the cassette portions 52, 54, the dampers 60, 62 apply a predetermined clamp load again the blade 28'. The predetermined clamp load squeezes the blade 28 between the dampers 60, 62. An example predetermined load is substantially equal to five Newtons (one pound) of force.

In one example, the tabs 90, 92 may extend into the connecting recess 94 or the connecting aperture 96 of the blade 28', 28" respectively, with the tabs 90, 92 being joined to each other to fix the cassette portions 52, 54 to each other relative to the proximal portion of the blade 28', 28". Alternatively, the connecting tabs 90, 92 may be longer for one of the cassette portions 52, 54 and may extend into and through the connecting recess 94 or the connecting aperture 96 and to the other cassette portion 54, 52 with the connecting tab 90, 92 being fixed to the other cassette portion 54, 52. The tabs 90, 92 may be fixed to the other cassette portion 54, 52, whether it is at an interface with a connecting tab 90, 92, or by engagement with a side of the shell 58, 56 of the other cassette portion 54, 52, by any known means, including but not limited to ultrasonic welding and adhesive bonding. The cassette portions 52, 54 may be joined at proximal tips 98, 100 thereof prior to positioning the cassette portions 52, 54 over the proximal portion 30'. In such an arrangement, the connections at the tips 98, 100 may serve as a living hinge between the cassette portions 52, 54 allowing the first cassette portion 52 to be slightly pivoted relative to the second cassette portion 54 and slipped over the proximal portion 30'. Once so positioned, the tabs 90, 92 may be joined to the shell 58, 56 of the opposing cassette portion 54, 52. When the cassette portions 52, 54 are properly positioned, the dampers 60, 62 are compressed by their respective shells 56, 58 to provide a preload against the proximal portion 30' of the blade 28', and the cassette portions 52, 54 are fixed to each other at the tabs 90, 92. An example preload may be approximately five newtons of force.

Figure 12:
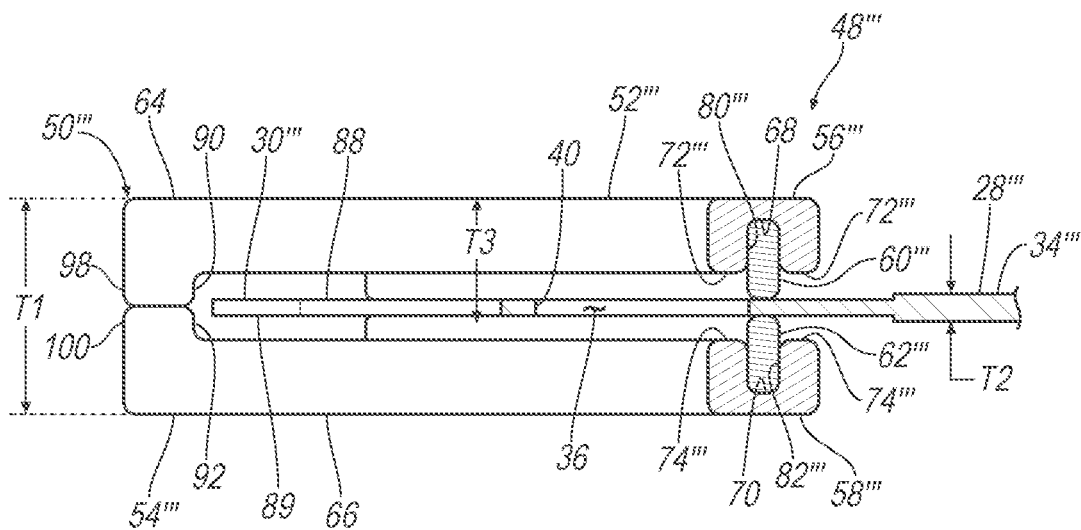
FIG. 12 is a sectional side view of an alternative example blade cartridge to that of FIG. 7.
Figure 13:
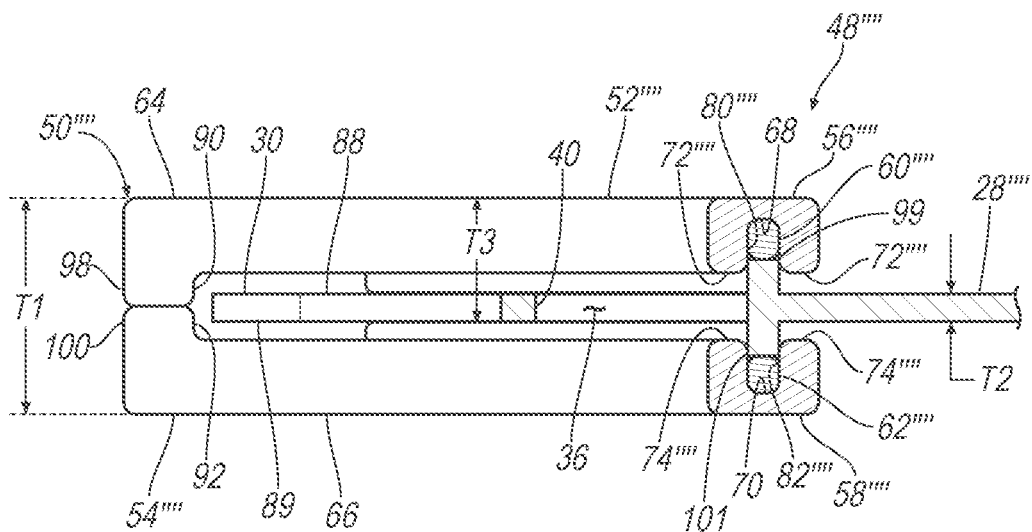
FIG. 13 is a sectional side view of another alternative example blade cartridge to that of FIG. 7.
Figure 14:
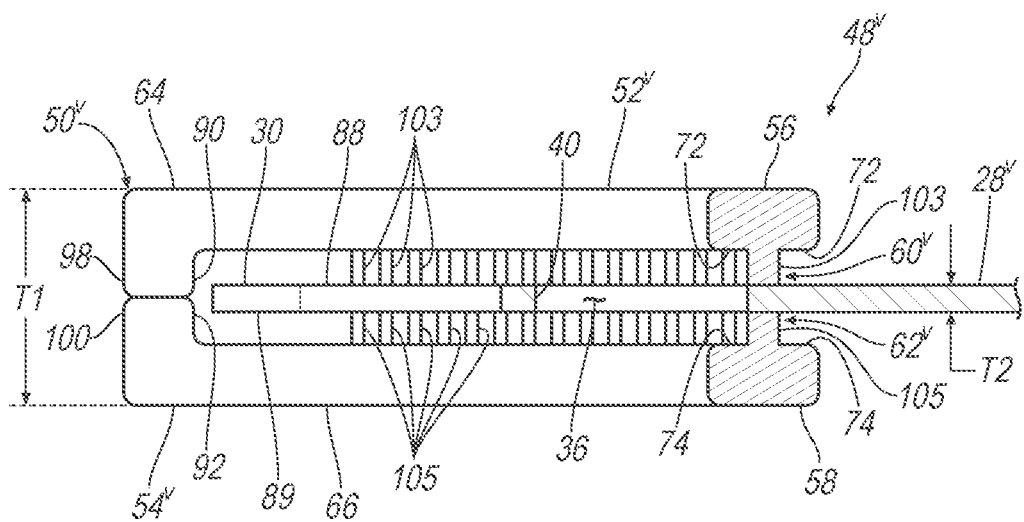
FIG. 14 is a sectional side view of yet another alternative example blade cartridge to that of FIG. 7.

FIGS. 12-14 illustrate alternative cassette configurations.

In FIG. 12, a saw blade cartridge 48" includes a dual-thickness saw blade 28" having a proximal portion 30''' thinner than a blade body 34'. The proximal portion 30''' is disposed between opposed cassette portions 52''', 54''' of a cassette 50'''. For the cassette 50" to develop the same preload against the proximal portion 30''' as that developed by the cassette 50 against the proximal section 30, several options are available. One example illustrated in FIG. 12 is to use shells 56''' and 58''' identical to the shells 56 and 58 and make dampers 60''' and 62" longer than dampers 60 and 62 to compensate for the thinner proximal portion 30'''. One configuration, not illustrated, includes forming the shells 56''' and 58' with shallower receiving pockets 80''' and 82" and making the dampers 60''' and 62" the same length as the dampers 60''' and 62". Another configuration, not illustrated, includes forming the shells 56' and 58''' with a greatest thickness in the axial direction. The thicker shell 56''' would have a distance between a surface 64" and an edge 72" greater than a distance between the surface 64 and the edge 72, proportional to the difference between the difference in thickness between the proximal portion 30''' and the proximal portion 30. Likewise, the thicker shell 58''' would have a distance between a surface 66" and an edge 74" greater than a distance between the surface 66 and the edge 74, proportional to the difference between the difference in thickness between the proximal portion 30''' and the proximal portion 30. The dampers 60''' and 62''' would be the same as the dampers 60 and 62. The alternatives described in this paragraph are exemplary and not comprehensive.

In FIG. 13, a saw blade cartridge 48"" is shown with a proximal portion 30"" of a saw blade 28"" including a first ridge 99 on a top surface 88"" and extending thereabove, and an aligned second ridge 101 on a bottom surface 89"" extending thereabove. The ridges 99 and 101 extend into, respectively, a first receiving pocket 80"" of the first shell 56"" and a second receiving pocket 82"" of the second shell 58"". The shells 56"" and 58"" may be the same as the shells 56 and 58. Cassette portions 52"" and 54"" of a cassette 50"" include, respectively, a first damper 60"" and a second damper"". The dampers 60"" and 62"" are shorter than the dampers 60 and 62 and do not extend beyond the respective inner edges 72"" and 74"" of the shells 56"" and 58"". The ridges 99 and 101 may be continuous, presenting a continuous surface for receipt by the receiving pockets 80"" and 82"" and engagement against the dampers 60"" and 62"" for the arc α. Alternatively, the ridges 99 and 101 may be tooth-shaped, presenting a plurality of teeth for receipt by pockets 80"" and 82"" and engagement against the dampers 60"" and 62"". Yet alternatively, the ridges 99 and 101 may be sinusoidally wave-shaped, presenting a plurality of undulations for receipt by pockets 80"" and 82"" and engagement against the dampers 60"" and 62"". The ridges 99 and 101 may also be formed separately from the blade 28"" and connected thereto by any suitable means, including but not limited to adhesive bonding, welding, and complementary shaped engagement features such as pins and receiving apertures. Even if formed separately, once connected to the blade 28"", the ridges 99 and 101 comprise part of the blade 28"". The alternatives described in this paragraph are exemplary and not comprehensive.

In FIG. 14, a saw blade cartridge 48$^V$ is shown with a saw blade 28$^V$ substantially identical to the saw blade 28'. The cassette 50$^V$ includes first and second cassette portions 52$^V$ and 54$^V$ made entirely of a first material. Each cassette portion 52$^V$ and 54$^V$ includes a damper 60$^V$ and 62$^V$ that comprises a plurality of axially extending digits 103 and 105 respectively. The axially extending digits 103 and 105 are formed of the first material and may be in the form of a plurality of axially extending tabs 103 and 105, or, alternatively a plurality of bristles (not illustrated), or a plurality of digits of any other suitable, axially extending shape. The length of the digits 103 and 105 is selected to achieve a desired preload against the blade 28$^V$. A desired stiffness of the dampers 60$^V$ and 62$^V$ may be established by selecting the dimensions and quantity of the digits 103 and 105. The alternatives described in this paragraph are exemplary and not comprehensive.

The coupler 26 facilitates installation and removal of each of the blades 28 and the cartridges 48, 48", 48"", 48$^V$ from the saw 22. Reference below to the cartridge 48 is inclusive of all of the cartridges 48, 48", 48"", 48$^V$.

The coupler 26, disposed at a distal end of the example handpiece 24, defines an axis of rotation 102. The mount axis 38 of the saw blade 28 and of the cartridge 48 is substantially aligned with the axis of rotation 102 when the saw blade 28 is mounted in the coupler 26.

The coupler 26 may include a coupler housing 104, a coupler cap 106, a coupler driver 108, a coupler pin 110, a coupler cup 112, a coupler bearing 114, a release button 116, and a coupler spring 118. The pin 110 may include a radially extending pin collar 120.

The housing 104 may include a housing head 122 at a most distal end thereof. The housing head 122 may have a pivot bore 124 therethrough, defining the axis of rotation 102 of the coupler 26. The coupler cup 112 may be pivotably disposed within the pivot bore 124. The bearing 114 may be radially disposed between a sleeve 128 of the cup 112 and the bore 124. The bearing 114 may be of any conventional construction, and may, by way of example, include an inner race, an outer race, and a plurality of rollers disposed therebetween. The cup 112 may include a lower lip 130 that extends radially outwardly from a lower end 132 of the cup 112, preventing travel of the cup 112 through the bore 124 in an upward axial direction. An upper end 134 of the cup 112 and the sleeve 128 may be received by and engaged by a driver bore 136 of the driver 108, with a press-fit between the driver bore 136 and the cup's sleeve 128 being an exemplary method of fixing one to the other. Any suitable alternative means to a press-fit for fixing the cup 112 in the bore 136 may be employed. The cup 112 may extend axially downwardly from a second side 135 of the driver 108 and into the pivot bore 124. Possible alternatives include, by way of example and not limitation, a threaded connection, adhesive bonding, and welding. The engagement between the driver 108 and the cup 112 prevents travel of the cup 112 through the bore 124 in a downward direction. With the driver 108 so fixed to the cup 112 for unitary movement therewith, the driver 108 may unitarily pivot about the axis of rotation 102 with the cup 112. The cup 112 and the driver 108 may alternatively be formed as a single, integral unit. In one example alternative construction, the lip 130 may be formed as a ring that is fixed to a lower end of the cup 112. Means of fixing may include, but are not limited to, threads, press-fit, welding, and adhesive bonding.

The coupler pin 110 may be slidably disposed within the cup 112 and the pivot bore 124 for axial translation therein along the axis of rotation 102. The collar 120 of the pin 110, or at least an inner portion of a collar larger than the illustrated collar 120, may be disposed within the driver 108, and above the cup 112 in a retaining position. The collar 120 may be of a larger diameter than an opening of the cup 112. Engagement of the collar 120 against the upper end 134 of the cup 112 may limit downward travel limit of the pin 110 relative to the cup 112. However, the downward travel of the pin may alternatively be limited by engagement of the cap against, for example, the blade 28 or the cartridges 48 or blade engagement prongs 137, such prongs discussed in more detail below.

The release button 116 is disposed at a lower end of the pin 110 and may be unitarily fixed to the lower end of the pin 110. The button 116 may be fixed to the pin 110 by means of a press-fit, or by welding, or by adhesive, or by threading, or by any alternative known means. The coupler spring 118 may be disposed within an annular void between an inner diameter of an inside wall surface 188 the cup 112 and an outer diameter of the pin 110. The inside wall surface 188 of the cup may have a first portion 138 larger in diameter than a second portion 140. The first portion 138 may be disposed at a lower end of the cup 112, below the second portion 140. The first portion 138 may be consistent with a counter bore, defining a step surface 142 between the first portion 138 and the second portion 140.

Figure 2:
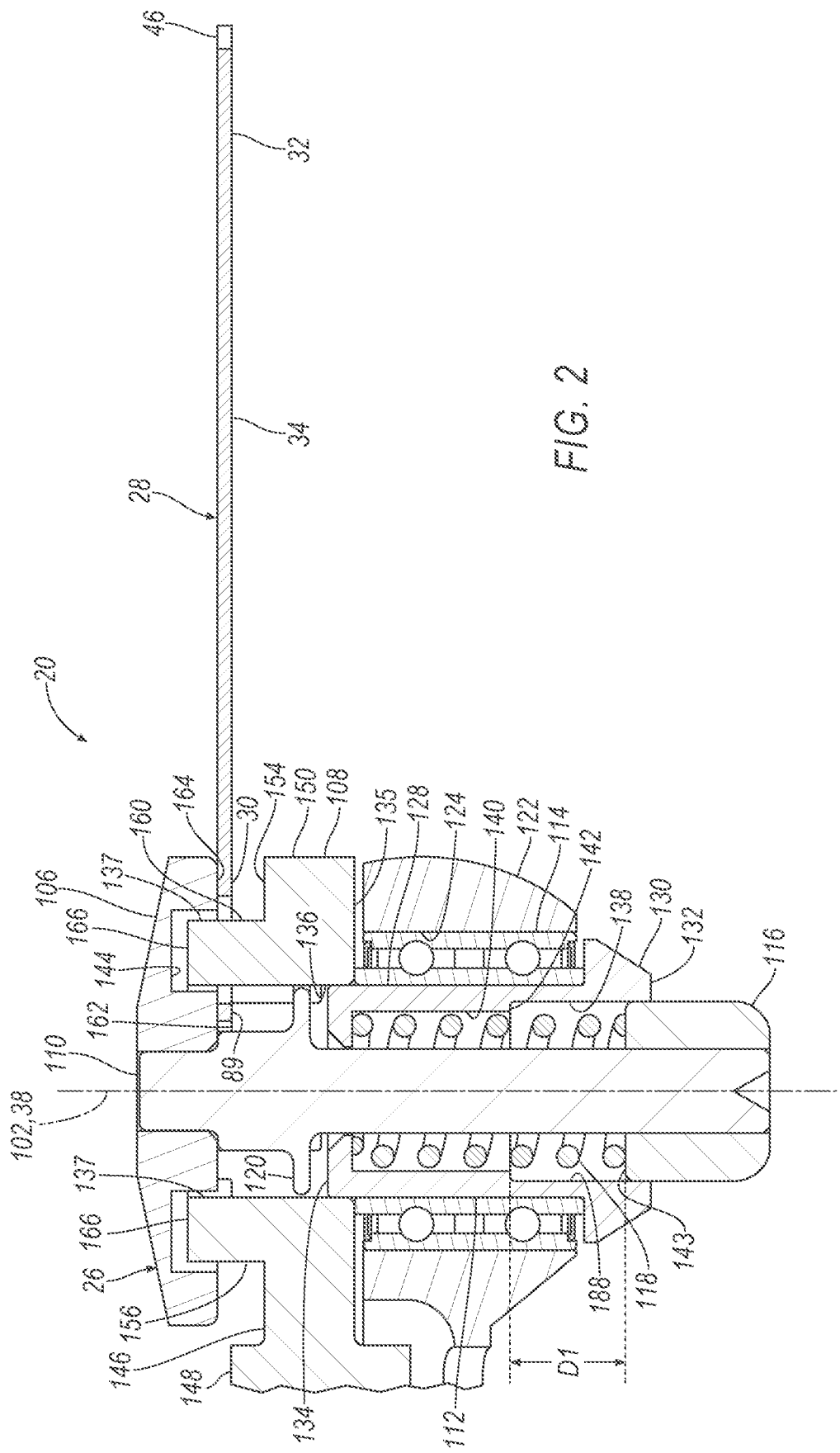
FIG. 2 is a sectional side view of the example coupler and blade of FIG. 1 through plane 2 in the direction of arrows 2A.

The first portion 138 accommodates travel of the button 116 into the lower end of the cup 112 for a distance D1. Given that the release button 116 and the pin 110 move as a unit, a full displacement position of the button 116 establishes a full displacement position of the pin 110. The distance D1 that is available for selective axial displacement of the button and the pin 110 relative to the cup 112 equals a distance from an upper engagement surface 143 of the release button 116 to the step surface 142. The distance D1 may be limited by an axial location of the step surface 142 which is engaged by the button 116 at a full displacement position of the button 116. When there is engagement between the upper engagement surface 143 of the button 116 and the step surface 142, the travel of the pin 110 and the button 116 is at its limit, and the additional available distance D1 equals zero. Downward travel of the pin 110 and the button 116 may be limited by engagement between the cap 106 and the driver 108, or alternatively, as noted above, by engagement between the collar 120 and the upper end 134 of the sleeve 128 of the cup 112. Should the collar 120 include webs, travel may be limited by engagement between the webs and the driver 108. As illustrated in FIG. 2, the available distance D1 is not quite at its maximum, as the presence of the blade 28 in the coupler 26 decreases the distance D1 by at least the thickness T2 of the blade. Movement of the release button 116 and the pin 110 relative to the cup 112 substantially equals movement of the button and pin 110 relative to and any of the driver 108 and the housing head 122, as each are substantially axially fixed to the cup 112.

The cap 106 is fixed to an upper end of the pin 110 and translates both axially and pivotally therewith. The cap 106 may be fixed to the pin 110 by means of a press-fit, or by welding, or by adhesive, or by threading, or by any alternative known means. Yet alternatively, the cap and pin may be formed as a single, integral unit. The cap 106 has a circumferential groove 144, or, alternatively, a plurality of circumferentially distributed cap apertures (not shown), that may receive the prongs 137, fixed to or part of the driver 108, when the coupler 26 is in a closed position. The prongs 137 may be on and may axially extend from an upper or first side 146 of the driver 108. The closed position may be alternatively referenced to as a first retaining position. The closed position is illustrated in FIG. 2. The coupler 26 may effectively retain blades 28 without the provision of the groove 144 in the cap 106, if, by way of example, the prongs 137 are no longer than the thickness of the blade 28. When the coupler 26 is used to retain the cartridge 48, the prongs would need to reach into the apertures 40 of the blade 28'. Providing the groove 144 in the cap 106 beneficially allows the same coupler 26 to retain both blades 28 and cartridges 48, as prongs 137 sufficiently long for use with cartridges 48 would prevent adequate clamping of blades 28 without the extra travel of the cap allowed by the groove 144.

The driver 108 may include a unitary driven portion 148, shown in part, and a driver locking portion 150. The driven portion 148 may be engaged by a linkage (not shown) with a drive motor (not shown) to achieve selective actuation of pivoting of the driver 108 about the axis of rotation 102. The linkage and the drive motor may both be disposed within the handpiece 24.

The driver locking portion 150 may include the prongs 137 which may be circumferentially distributed about the axis of rotation 102. The driver locking portion 150 may have a base 158 having an upper surface 154 on the first side 146 that is substantially planar in shape. A raised section 160 may extend upwardly from the upper surface 154. The raised section 160 may be segmented into a plurality of raised sections 160, for example four raised sections 160. Each raised section 160 may have a substantially arcuate shape. The raised sections 160 may be evenly circumferentially distributed about the axis of rotation 102. The raised sections 160 may be centered around the axis of rotation 102. The prongs 137, as illustrated, may be integral with and extend upward from each end of each raised section 160, an example number of prongs being eight. Each raised section 160 may have an engaging surface 162 disposed between the prongs 137. Alternatively, the prongs 137 may entirely comprise the raised sections with engaging surfaces 162 disposed therebetween.

Figure 4:
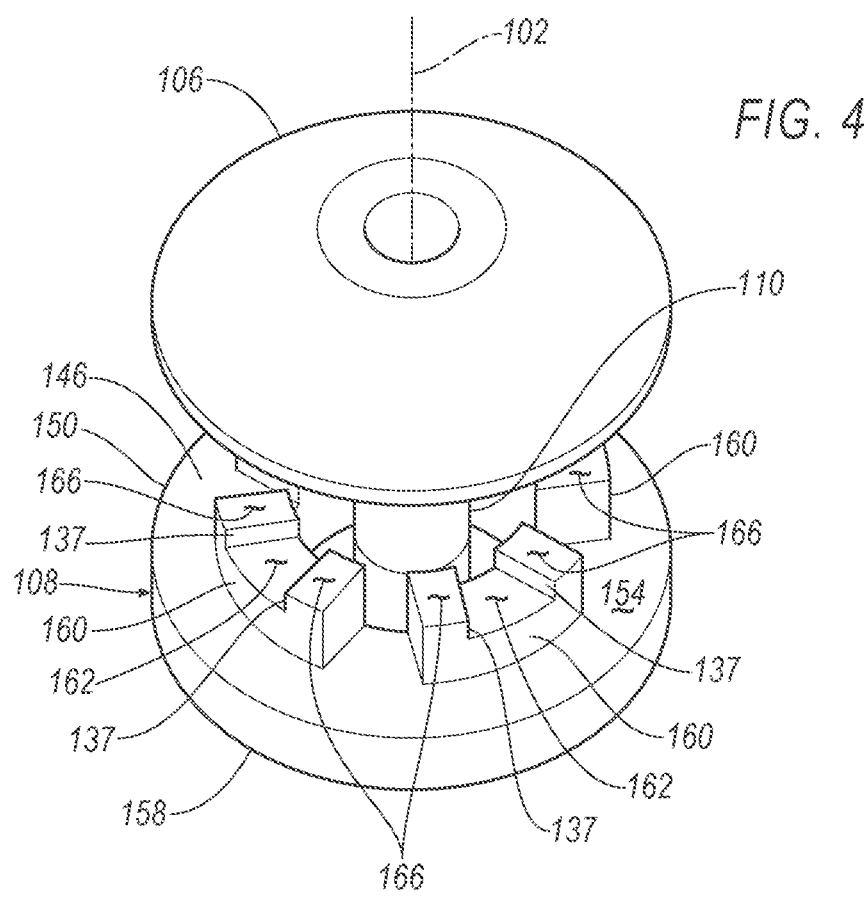
FIG. 4 is a perspective view of a portion of the example coupler of FIG. 1 in an open position.

With the coupler 26 in the closed position, the prongs 137 of each of the raised sections 160 extend at least in part past the collar 120 of the pin 110, and may be received by the groove 144 in the cap 106. In an open position as shown in FIG. 4, there is an axial gap between the top surfaces 166 of the prongs 137 and the bottom side 164 of the cap 106 greater than the thickness T2 of the proximal portion 30 of blade 28 to allow receipt of the blade 28 between the top surfaces 166 of the prongs 137 and the bottom side 164. The cap 106 and the bottom side 164 thereof may be biased by the spring 118 toward the engaging surface 162 of the raised section 160 to clamp the proximal portion 30 therebetween when the button 116 is released.

The collar 120 as shown in the figures may be entirely disposed within the driver bore 136. A similarly configured coupler, described and illustrated in the earlier-referenced U.S. Pat. No. 7,833,241B2, includes a collar having an inner portion similar to the present collar 120, but with a ring-like outer portion connected to the inner portion by a plurality of webs. The webs and the outer portion are helpful in removing blades from the coupler. While not illustrated herein, the present collar 120 may also include such webs, and yet alternatively, may also include such an outer portion and such outer portion may be disposed radially inwardly of the shells 56, 58.

The saw blade 28 of FIG. 3 may be received by the coupler 26 in the following way. The release button 116 is pushed, consistent with the orientation of FIG. 1 and FIG. 2, in an upward direction, against the bias of the coupler spring 118, displacing the cap 106 upwardly. When the button 116 is depressed, the axial gap D2 between the collar 120 and the cap, and more specifically, between a bottom side 164 of the cap 106 and a top surface 166 of the prongs 137, is greater than the thickness T2 of the proximal portion 30 of the blade 28, allowing the proximal portion 30 of the blade 28 to be inserted therein. The slot 42 in the proximal portion 30 may be tapered as illustrated, to aid in guiding the locating radial surface 44 into alignment with the coupler pin 110. A radius of each of the pin 110 and the radial surface 44 may be substantially the same to facilitate an alignment of axes 38, 102. The blade 28 may be aligned to a desirable orientation, for example, aligning the blade 28 longitudinally in parallel with the handpiece 24, in accord with the illustrations. The blade 28 may be rotatively pivoted very slightly about the axis of rotation 102 relative to the coupler 26 as the button 116 is released to align the prongs 137 of the driver locking portion 150 with the apertures 40 of the proximal portion 30 of the blade 28. With the blade apertures 40 in receipt of the prongs 137 and the button 116 released, the top surface 88 of the proximal portion 30 of the blade 28 is engaged by the bottom side 164 of the cap 106. The bottom surface 89 of the proximal portion 30 is accordingly pressed against the engaging surface 162 of the raised section 160. locking portion 150. A clamping force of the cap 106 against the proximal portion 30 of the blade 28, and in turn against the upper surface 154 of the locking portion 150 is provided by the coupler spring 118. Once the blade 28 is clamped within the coupler 26, the saw 22 may be actuated by energizing the motor to pivotably reciprocate the saw blade 28, and the saw system 20 may be used to cut material. Driving of the blade 28 may rely on engagement of the prongs 137 against the driving surfaces 36.

To release the blade 28, the release button 116 is pressed upward against the bias load of the spring 118. The pin moves upward, and with it the collar 120 and the cap 106. The blade may be withdrawn from the coupler 26 as soon as the gap D2 between the top surfaces 166 of the prongs 137 and the bottom side 164 of the cap 106 that is greater than the thickness T2 of the blade 28. With further pressing of the button 116 providing additional pin displacement, the collar 120 may aid in the removal by pushing the proximal portion 30 of the blade 28 past the prongs 137. Engagement between the collar 120 and the proximal portion 30 may occur within a radius inside of the apertures 40 of the blade 28.

The saw blade cartridge 48 of FIGS. 5-9 may be received by the coupler 26 in the following way. The release button 116 is pushed, consistent with the orientation of FIG. 5 and FIG. 6, in an upward direction, against the bias of the spring 118, displacing the cap 106 upwardly. When the gap D2 between the bottom side 164 of the cap 106 and the top surface 166 of the prongs 137 is greater than a thickness between the bottom surface 89 of the blade 28' and the outer side 58 of the first shell 56, the proximal portion 30' of the blade cartridge 48 may be inserted into and received by the coupler 26. The slot 42 may be tapered as illustrated, to aid in guiding the locating radial surface 44 into alignment with the coupler pin 110. The blade 28' may be aligned to a desirable orientation, for example, aligning the blade 28' longitudinally in parallel with the handpiece 24, in accord with the illustrations. The blade 28' may be rotatively pivoted very slightly about the axis of rotation 102 relative to the coupler 26 as the button 116 is released to align the prongs 137 of the driver locking portion 150 with the apertures 40 of the proximal portion 30' of the blade 28' of the blade cartridge 48. With the blade apertures 40 in receipt of the prongs 137 and the button 116 released, the cassette 50 of the cartridge 48 is pressed by the bottom side 164 of the cap 106 against the upper surface 154 of the locking portion 150. A clamping force of the cap 106 against the outer side 64 of the first cassette portion 52, and in turn of the outer side 66 of the second cassette portion 54 against the upper surface 154 of the locking portion 150 of the driver locking portion 150 is provided by the coupler spring 118. Once the blade 28' is clamped within the coupler 26, the saw 22 may be actuated by energizing the motor to pivotably reciprocate the saw blade 28', and the saw system 20 may be used to cut material. As with the blade, driving of the cartridge 48 may rely on engagement of the prongs 137 against the driving surfaces 36.

To release the cartridge 48, the button 116 may be pressed upward by a user's selective engagement of a finger or a thumb against the load of the coupler spring 118. The pin moves upward, and with it the collar 120 and the cap 106. The cartridge 48 may be withdrawn from the coupler 26 as soon as there is a gap between the top surfaces 166 of the prongs 137 and the bottom side 164 of the cap 106 that is greater than a thickness T3 between the bottom surface 89 of the blade 28' and the outer side 64 of the first shell 56.

A second example coupler 26' provides a position lock 168, shown in FIGS. 15-28, for avoiding unintended opening of the coupler 26'. The position lock 168, as described in more detail below, beneficially prevents unintended opening of the coupler 26' and accordingly prevents untended losses of both cartridges 48 and blades 28 from the coupler 26' during operation of a yet alternative saw system 20'. Such unintended opening may occur with the coupler 26 when a downward or upward load on the blade 28 parallel to but distal to the axis 38 is applied. Such a load may pivot the blade within the coupler 26 if the load is sufficient to overcome the clamping load of the coupler spring 118. In such a case, the cap 106 may be deflected upwardly, away from the driver 108, allowing the blade 28 or the cartridge 48 to escape the prongs 137 and thus escape the coupler 126. The position lock 168 of the coupler 26' prevents such escapes. The coupler 26' is substantially the same as the coupler 26, except for the inclusion of the position lock 168, consistent with the description below.

Figure 15:
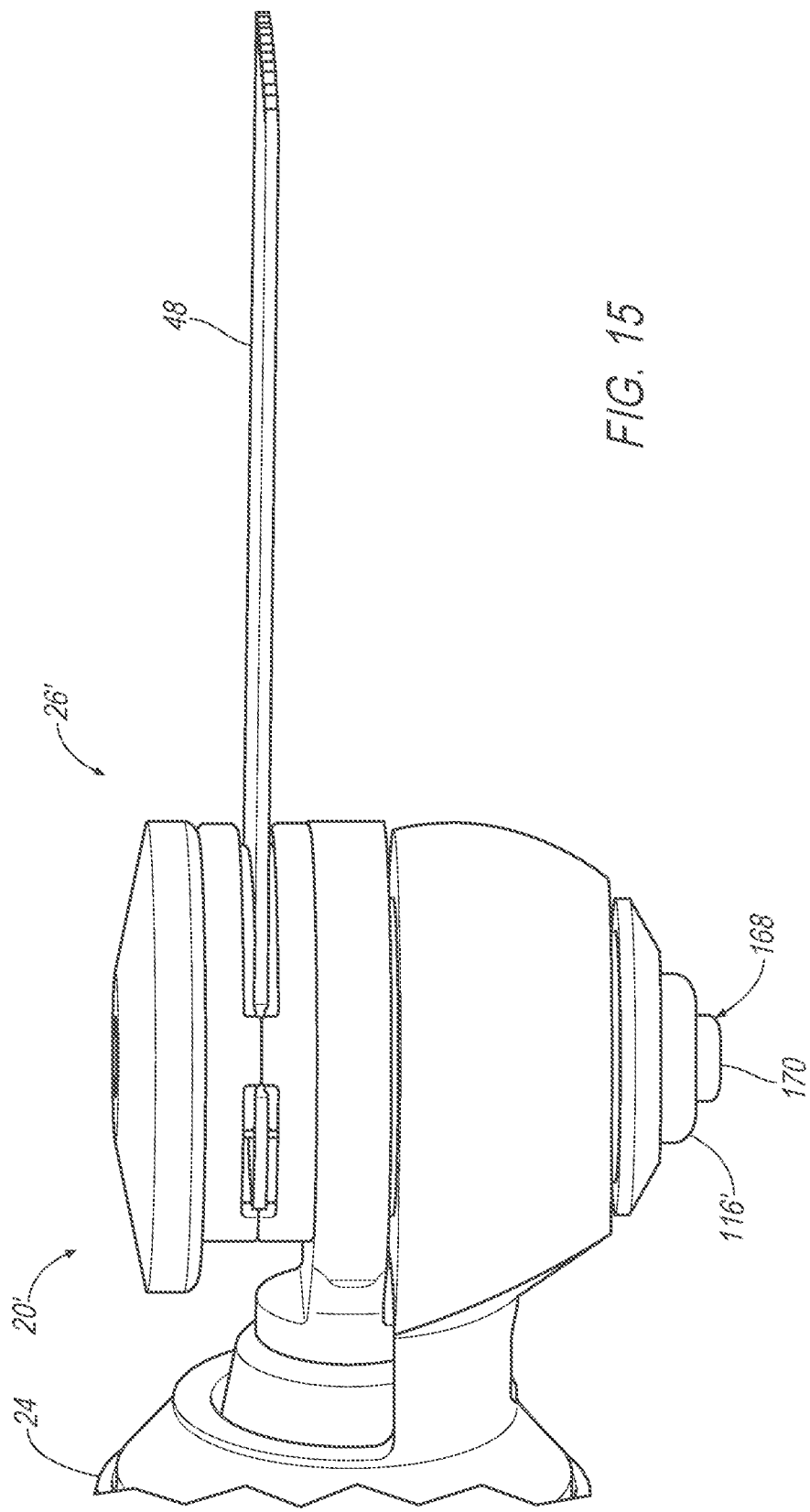
FIG. 15 is a perspective view of a distal portion of a handpiece including an alternative example coupler in receipt of an example saw blade cartridge.

FIG. 15 shows a distal portion of the handpiece 24 including the coupler 26' in receipt of the saw blade cartridge 48. A release button 116' is shown in the first retaining position and a lock button 170 is shown in a locked position.

Figure 16:
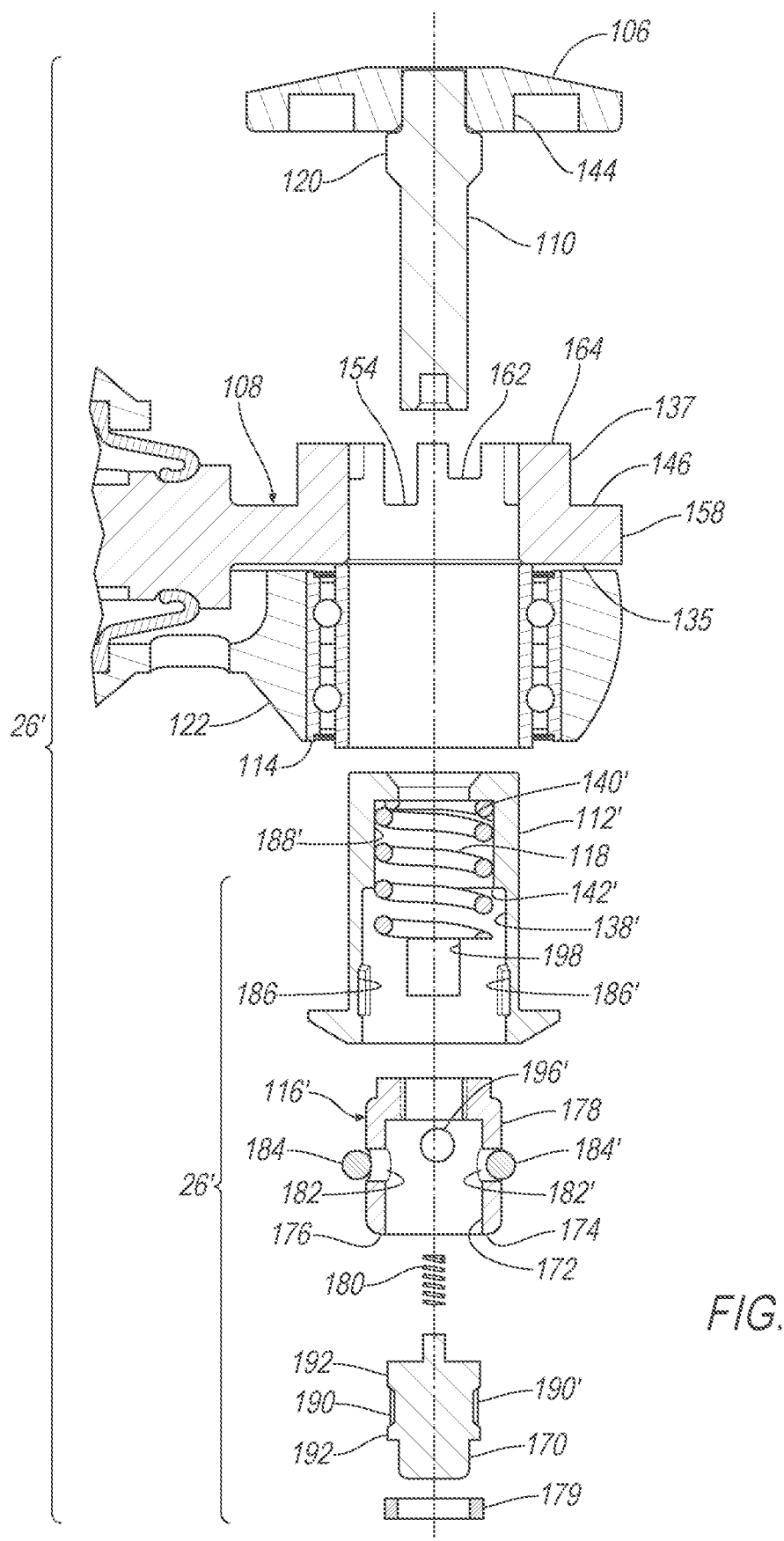
FIG. 16 is an exploded section view of the coupler of FIG. 15.

FIG. 16, an exploded section view, shows the many of the individual elements of the coupler 26'. Reference characters for components and elements of the coupler 26' are used consistently with respect to the use of the reference characters in the descriptions of the coupler 26. Components sharing a reference number but—for an apostrophe may be substantially similar, at least in function. In other cases, components and features sharing a reference number but—for an apostrophe may be identical to the other, but—for the location of the components and features. The coupler 26' is distinguished over the coupler 26 in that the coupler 26' includes the position lock 168, and provides the first retaining position and a second retaining position of the cap 106 relative to the driver 108 and the head 122 of the housing 104. The position lock 168 maintains the cap 106 in the first retaining position relative to the driver 108 and the head 122 when a blade 28 is engaged by the coupler 26'. The position lock 168 likewise maintains the cap 106 in the second retaining position relative to the driver 108 and the head 122 when the cartridge 48 is engaged by the coupler 26'. The cap 106, when in the second retaining position, is more axially removed from the engaging surface 162 than when in the first retaining position.

The position lock 168 may be combined with a release button 116'. The position lock 168 includes the lock button 170. The lock button 170 is slidably disposed within the release button 116'. More specifically, the release button 116' may have formed therein a lock cavity 172 in which the lock button 170 may be slidably disposed. The lock cavity 172 may be open on the lower end 174 of the button 116'. The lower end 174 of the button 116' is alternatively identified herein as a first end 174 of the button 116', and the first end 174 of the button wall 176. The button wall 176 is bounded by and between the lock cavity 172 and the outer surface 178 of the release button 116'. The button wall 176 may be substantially cylindrical. The lock button 170 may be retained within the lock cavity 172 by a retaining ring 179 disposed at an end of the lock cavity 172. The ring 179 may be retained in the lock cavity 172 by any known means, including by way of example and not limitation, press-fit, welding, and adhesive bonding. Alternative means of retention of the lock button 170 may also be employed, including a snap ring, peening of an end of first end 174 of the button 116, 3D forming of both the lock button 170 and the release button 116' with the lock button formed to be slidably disposed in the cavity 172, and so on.

The position lock 168 may further include a lock spring 180 disposed between the lock button 170 and the coupler pin 110. Alternatively, given that the release button 116' is fixed to the coupler pin 110, the lock spring could be disposed between the lock button and the release button 116'. The lock spring 180 biases the lock button 170 downwardly relative to the pin 110 and the release button 116', toward the locked position. As the coupler pin 110 is fixed to each of the release button 116' and the cap 106, the lock button 170 is biased downwardly relative to those as well. The lock button 170 extends beyond the first end of the button wall 176, in the locked position, and may be substantially flush with the first end 174 of the button wall 176 in an unlocked position. Having the lock button 170 extend beyond the first end 174 in the locked position beneficially allows the lock button to be displaced further into the release button 116' for the purpose of releasing the blade 28 or the cartridge 48. Having the lock button 170 be flush with the first end 174 of the button wall 176 is not a necessary feature, but may beneficially provide the user with an indication that the lock button 170 has reached a full-travel position, and that no further force against the lock button 170 is needed to release the blade 28 or the cartridge 48.

A first slider aperture 182 is in slidable receipt of a first slider 184. The aperture 182 passes through the button wall 176 at a first axial and circumferential location of the wall 176. In all available positions of the release button 116' and the lock button 170, the first slider 184 remains at least in part in the first slider aperture 182. Example positions of the lock button 170 include the locked position and the unlocked position. Example positions of the release button 116' include the retaining position and the release position. The retaining and release positions of the button 116' occur simultaneously with the retaining and release positions of the cap 106 as both are unitarily connected by the pin 110 with all three parts 116', 106, 110 moving as a unit. The slider 184 moves substantially unitarily with the release button 116' in the axial direction, and is able to move in a radial direction along the aperture 182 relative to the wall 176. The first slider 184 is illustrated as being substantially a sphere in shape. However, other shapes may be employed. For example, the slider 184 may have an elongated shape, such as a cylinder (not illustrated). Such a cylinder may be radiused on each end, and may thus resemble a double-ended bullet. Forming the slider 184 to be spherical or to have spherical ends aids in preventing the slider 184 from unintentionally jamming the lock button 170 in an undesired position. The slider 184 may yet alternatively have tapered ends to prevent such jamming. Whether the slider 184 is spherical or cylindrical may depend on a ratio between a thickness of the wall 176 and a diameter of the slider 184. Independent of its shape, the slider 184 is rigid, being formed of relatively stiff material that substantially does not deform during its anticipated use. Example materials include steel and thermoplastic.

Figure 17:
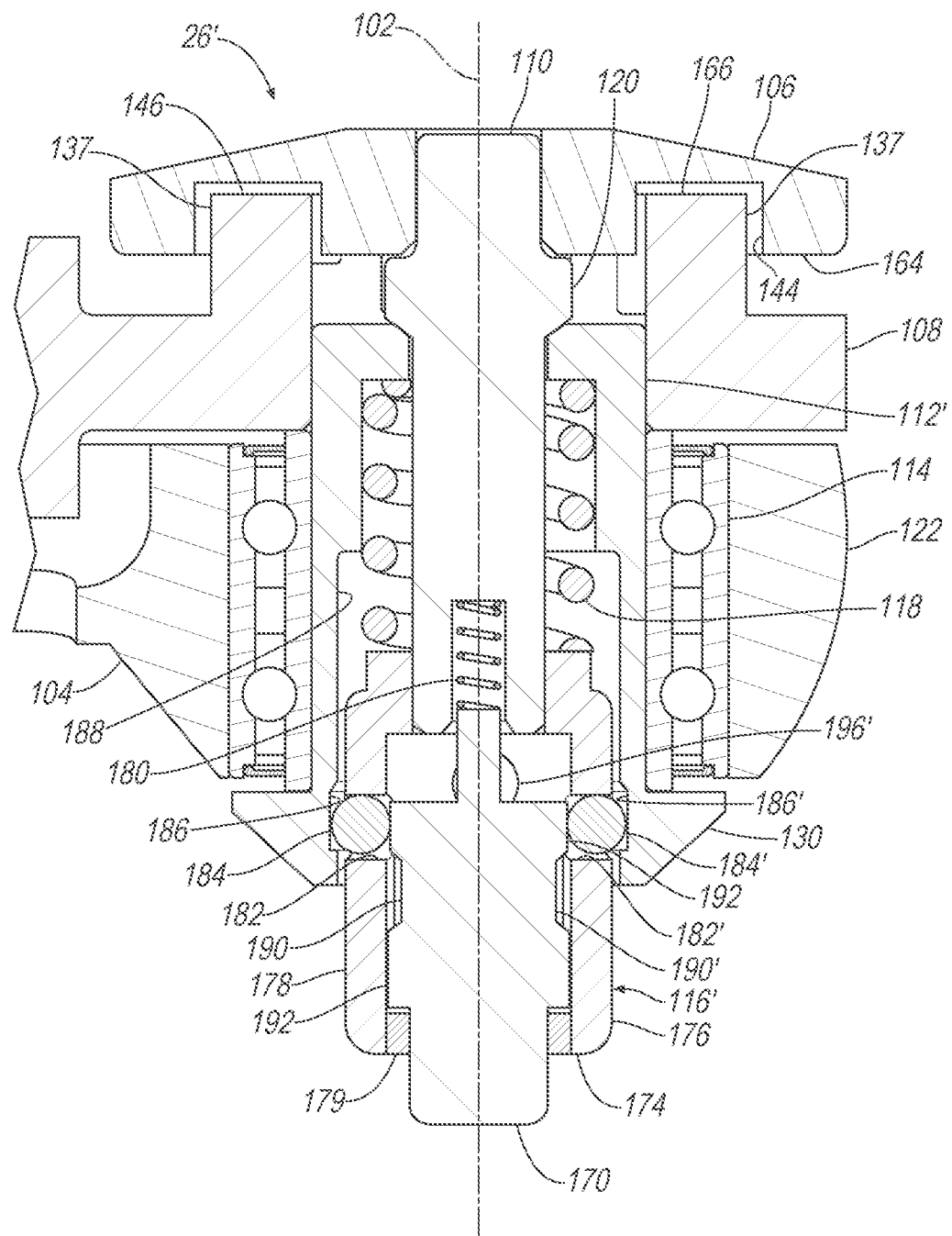
FIG. 17 is a sectional side view of the coupler of FIG. 15 without a blade.
Figure 18:
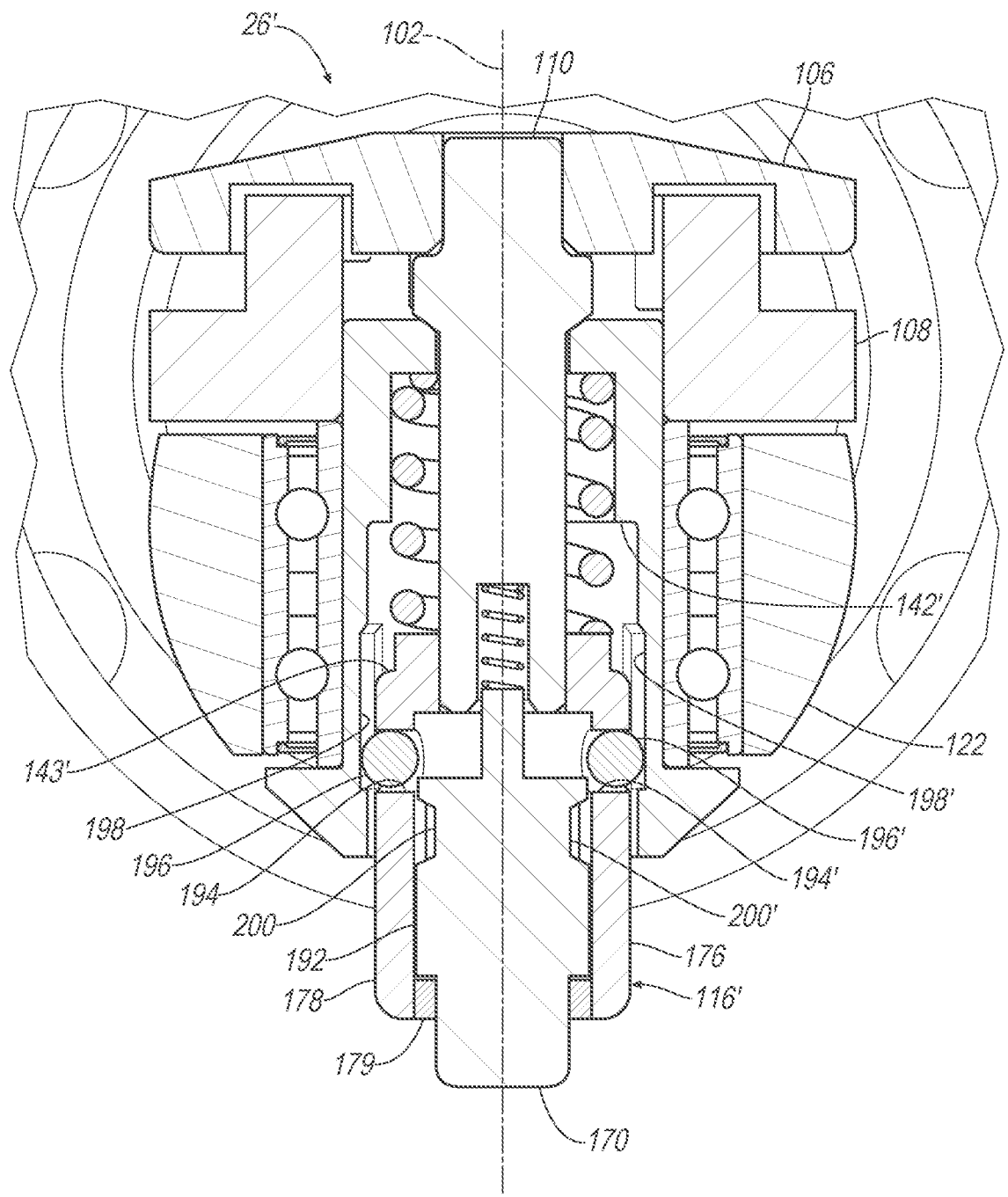
FIG. 18 is a sectional front view of the coupler of FIG. 15 without a blade.

FIGS. 17 and 18 show the release button 116' in the first retaining position and the lock button 170 in a first locked position.

As shown in FIG. 17, the position lock 168 further includes a first cup receiving notch 186 formed in an inside wall surface 188' of a coupler cup 112', and a first lock button receiving notch 190 formed in an outer surface 192 of the lock button 170. Like the inside wall surface 188, the inside wall surface 188' may have a first portion 138' larger in diameter than a second portion 140'. The first portion 138' may be disposed at a lower end of the cup 112', below the second portion 140'. The first portion' 138 may be consistent with a counter bore, defining a step surface 142' between the first portion 138' and the second portion 140'. The slider 184 may, under certain conditions explained in more detail below, be received in part by the first cup receiving notch 186 and by the first lock button receiving notch 190 when the notches 186, 190 are aligned with the slider aperture 182. An identical or twin first slider 184' may be located in a twin aperture 182' located 180 degrees from the first slider 184 for engagement with a mirror image first cup receiving notch 186' and a mirror image first lock button receiving notch 190'.

A second slider aperture 194 is in slidable receipt of a second slider 196. The aperture 194 passes through the button wall 176 at a second axial and circumferential location of the wall 176. In all available positions of the release button 116' and the lock button 170, the second slider 196 remains at least in part in the second slider aperture 194. The slider 196 moves substantially unitarily with the release button 116' in the axial direction, and is able to move in a radial direction along the aperture 194 relative to the wall 176. The second slider 196 may be, but need not be, the same shape and size as the first slider 184. The second circumferential location may be 90 degrees from the first circumferential location. That is, the second slider aperture 194 and slider 196, may be located 90 degrees from the first slider aperture 182 and the first slider 184.

As shown in FIG. 18, the position lock 168 also includes a second cup receiving notch 198 formed in the inside wall surface 188' of the cup 112'. The position lock 168 further includes a second lock button receiving notch 200 formed in the outer surface 192 of the lock button 170. The slider 196 may, under certain conditions explained in more detail below, be received in part by the second cup receiving notch 198 and by the second lock button receiving notch 200 when the notches 198, 200 are aligned with the slider aperture 194. An identical twin second slider 196' may be located in a twin slider aperture 194' located 180 degrees from the second slider 196 for engagement with mirror image second cup receiving notch 198' and a mirror image second lock button receiving notch 200'.

When the position lock 168 is in a locked condition, the lengths of the notches 186, 190, 198, 200 may allow some limited axial movement, but not release, of the blade 28 or cartridge 48.

FIGS. 17 and 18 show sectional views of the coupler 26' without a blade 28 or a cartridge 48 and in the closed or first retaining position of the release button 116' and the first locked position of the lock button 170. FIGS. 17 and 18 aid in illustrating how the position lock 168 is retained as part of the coupler 26'. The release button 116' is biased to the full extent of its downward available travel in the first portion 138 by the coupler spring 118 disposed between the cup 112' and the release button 116'. The release button 116' may be retained in the cup 112' by the first sliders 184, 184' which while remaining largely disposed within the second slider apertures 182, 182', and are partially disposed in the first cup receiving notches 186, 186'. The sliders 184, 184' are held in the notches by the outer surface 178 of the lock button 170. The lock button 170 is biased to its most downward position, the first locked position, as illustrated in FIGS. 17 and 18, by the lock spring 180. The retention of the lock button 170 within the engaging button may be achieved by engagement of the lock button 170 against the retaining ring 179.

Figure 19:
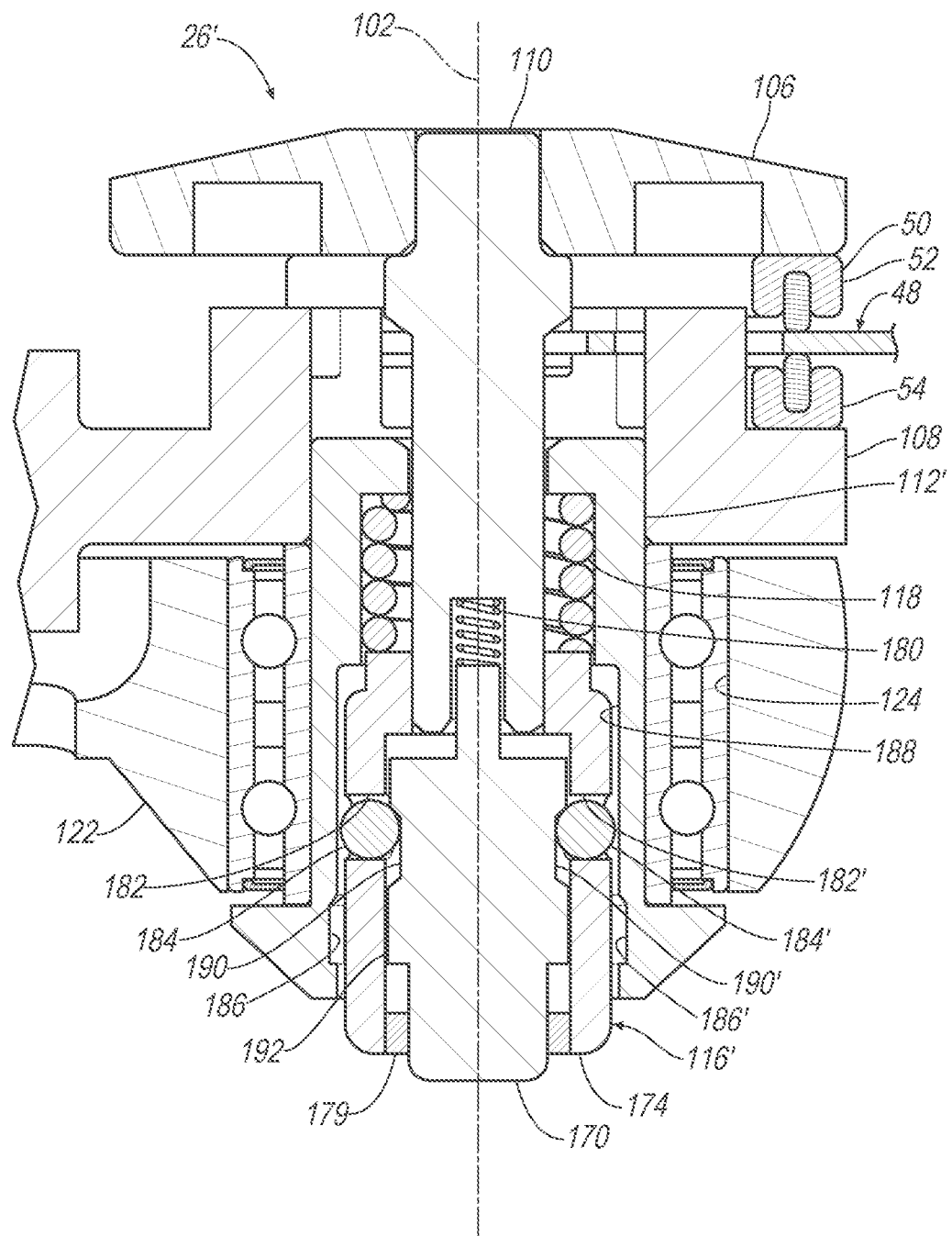
FIG. 19 is a sectional side view of the coupler of FIG. 15 holding an example blade cartridge with an example lock button in a locked position and with an example button and pin and cap in an example retaining position.
Figure 20:
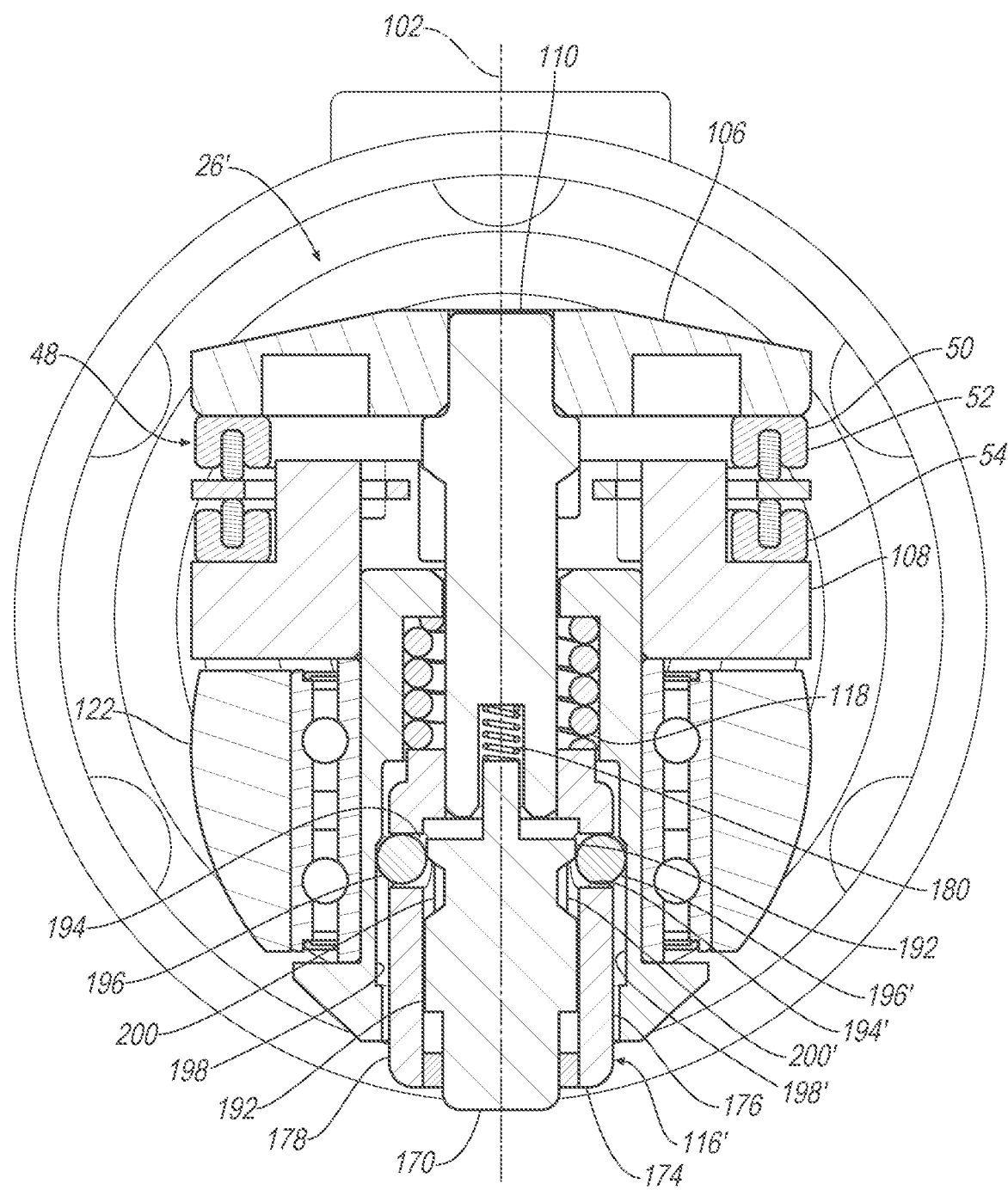
FIG. 20 is a sectional front view of the coupler of FIG. 15 holding the blade cartridge of FIG. 19 with the lock button in the locked position and the button and pin and cap in the retaining position.

FIGS. 19 and 20 show the release button 116' in a second retaining position and the lock button 170 in a second locked position. The second locked position of the lock button 170 is axially intermediate between the first locked position and the unlocked position.

FIGS. 19 and 20 provide sectional views of the coupler of FIG. 15 holding the example blade cartridge 48 with the lock button 170 in the second locked position and the example release button 116', pin 110, and cap 106 in the second retaining position. The lock button 170 extends beyond the first end 174 of the wall 176, indicating that the lock button is in the locked position. The first sliders 184, 184' are slidably disposed in their respective first slider apertures 182, 182'. The second sliders 196, 196' are slidably disposed in their respective second slider apertures 194, 194'. The first sliders 184, 184' are disposed in part in the first lock button receiving notches 190, 190', allowing the first sliders 184 to axially transit with the button 116 in the first portion 138 and along the inside wall surface 188' of the cup 112'. The second sliders 196, 196' are respectively disposed in part in the second cup receiving notches 198, 198'. The sliders 196, 196' are blocked from leaving the notches 198, 198' by engagement of the sliders 196, 196' against an upper part of the upper part of the outer surface 192 of the lock button 170. At the second retaining position of FIGS. 19 and 20, the sliders 196 and 196' are at or near engagement an upper end of the second lock button receiving notches 200, 200'. Any effort to displace the cap 106 and pin 110 any further in an upward direction is resisted by engagement of the sliders 196 and 196' against the respective ends of the notches 200, 200'. Such engagement resists any force against the cap 106 that might otherwise cause the cartridge 48 to become released from the coupler 26'.

Figure 21:
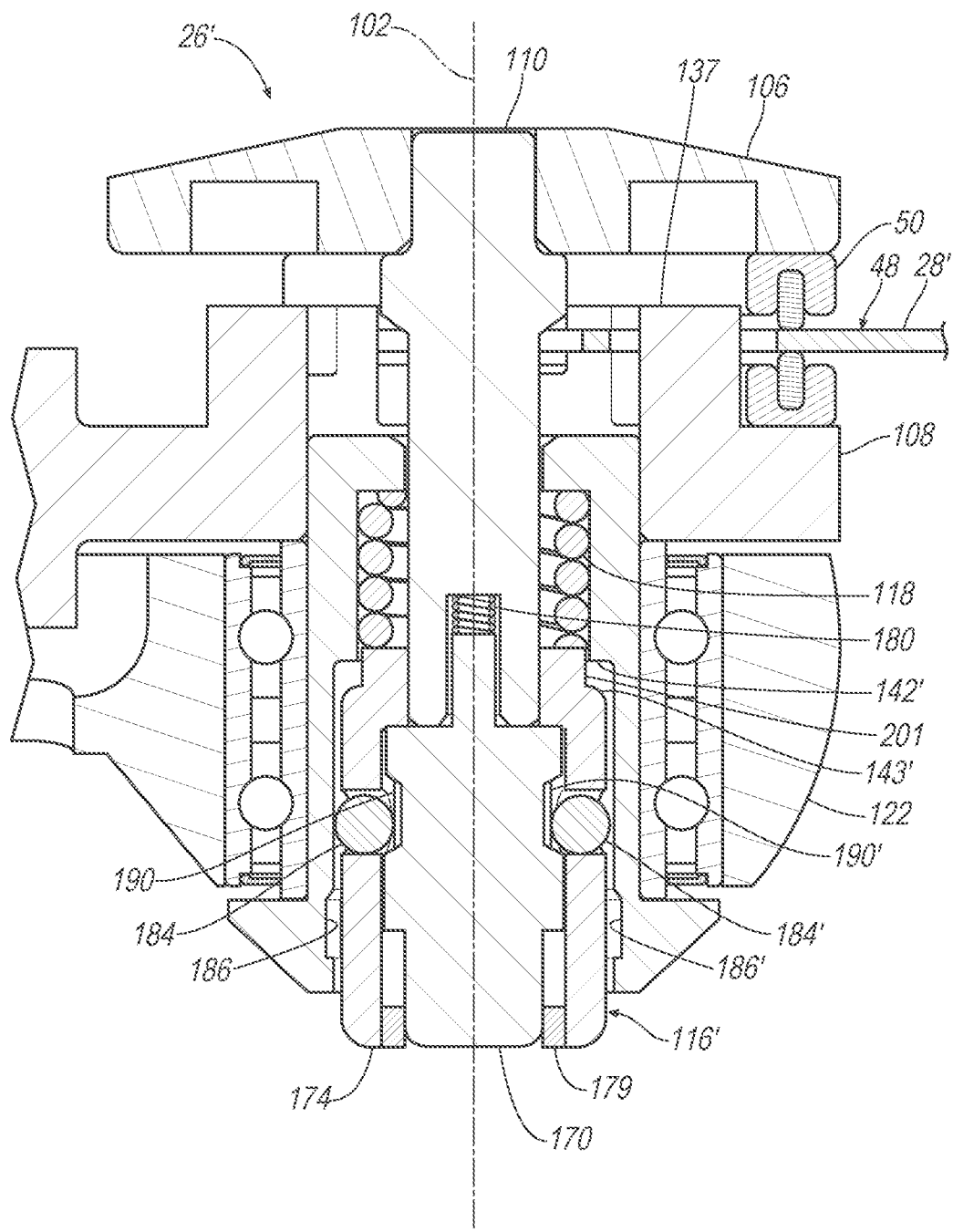
FIG. 21 is a sectional side view of the coupler of FIG. 15 holding the blade cartridge of FIG. 19 with the lock button in an unlocked position and the button and pin and cap in the retaining position.
Figure 22:
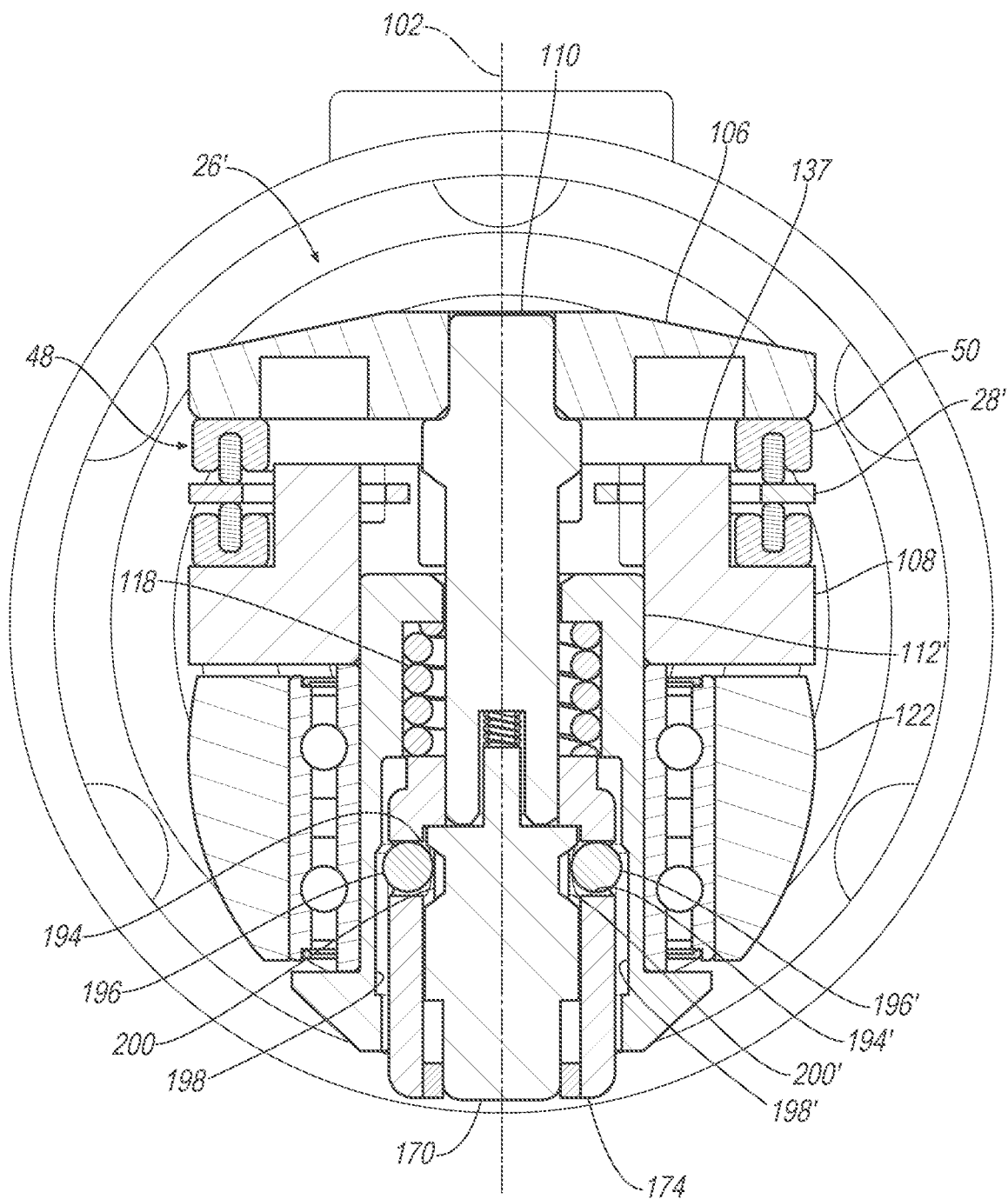
FIG. 22 is a sectional front view of the coupler of FIG. 15 holding the blade cartridge of FIG. 19 with the lock button in the unlocked position and the button and pin and cap in the retaining position.

FIGS. 21 and 22 show the coupler 26' and the cartridge 48 of FIGS. 19 and 20 in an unlocked and engaged condition, in which the lock button 170 is in the unlocked position and the release button 116' remains in the second retaining position with the blade 28' of the cartridge 48 remaining below the ends of the prongs 137. The lock button 170 may be moved to the unlocked position by a user applying a force against an exposed end of the lock button 170 to overcome the force of the spring 180. The lock button 170 in the unlocked position may be substantially flush with the end 174 of the button wall 176, evidencing that it is in the unlocked position. With the lock button 170 in the unlocked position, the second lock button receiving notches 200, 200' are aligned with the second slider apertures 194, 194', allowing the sliders 196, 196' to move radially inwardly for receipt by the notches 200, 200'. The release button 116' may thus be moved, against the force of the coupler spring 118 to a second release position as illustrated in FIGS. 23 and 24.

Figure 23:
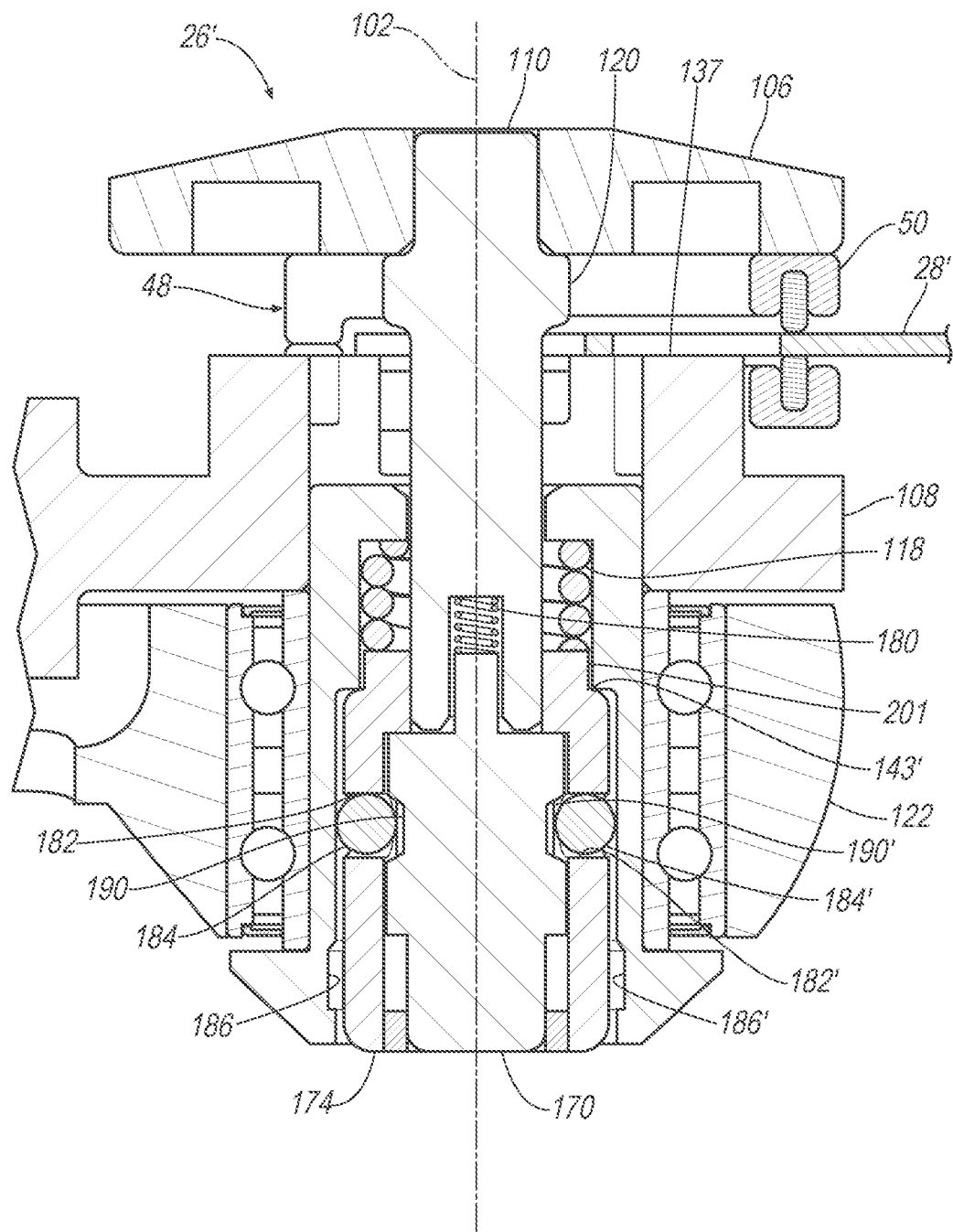
FIG. 23 is a sectional side view of the coupler of FIG. 15 holding the blade cartridge of FIG. 19 with the lock button in an unlocked position and an example button and pin and cap in an example release position.
Figure 24:
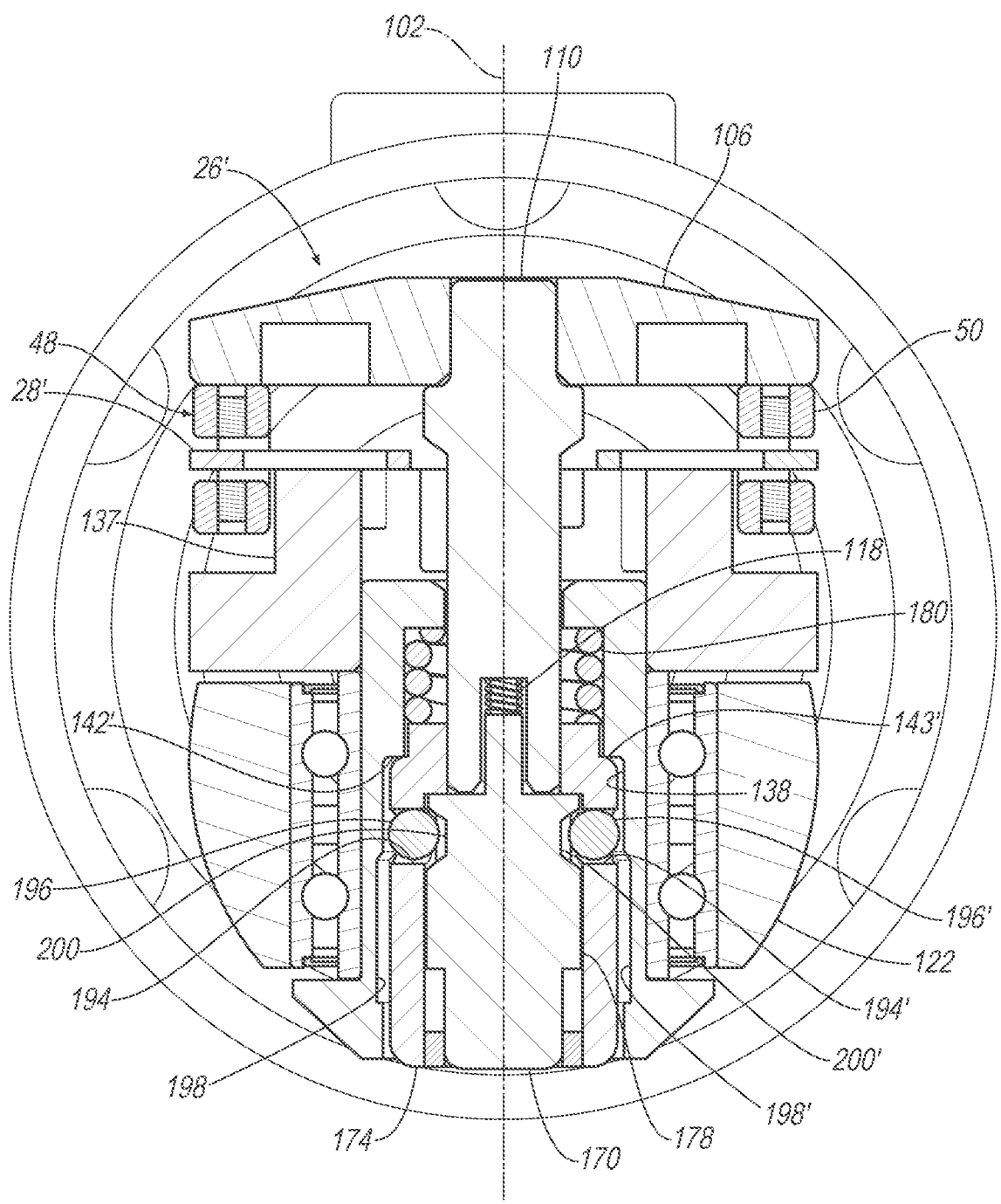
FIG. 24 is a sectional front view of the coupler of FIG. 15 holding the blade cartridge of FIG. 19 with the lock button in an unlocked position and an example button and pin and cap in an example release position.

FIGS. 23 and 24 show the coupler 26' and the cartridge 48 of FIGS. 19 and 20 in an unlocked and disengaged condition, in which the lock button 170 is in the unlocked position and the release button 116' has been moved upwardly against the force of the coupler spring 118 to the second release position. The unlocked and disengaged condition may be achieved by the selective engagement of the lock button 170 and then the release button 116' by a user's finger or thumb being pressed upwardly against the buttons 170 and 116'. In the second release position, the second sliders 196, 196' are disposed in part in the second lock button receiving notches 200, 200'. With the second sliders 196, 196' so positioned, the release button 116' is able to travel upward, responsive to user input, until an upper engagement surface 143' of the release button 116' is against the step surface 142' of the cup 112'. As illustrated, a pilot portion 201 of the release button 116' may extend upwardly beyond the upper engagement surface 143'. With a corresponding displacement of the cap 106, the cartridge 48 may be lifted upwardly, with the blade 28' being able to clear the prongs 137, permitting removal of the cartridge 48 from the coupler 26'.

Figure 25:
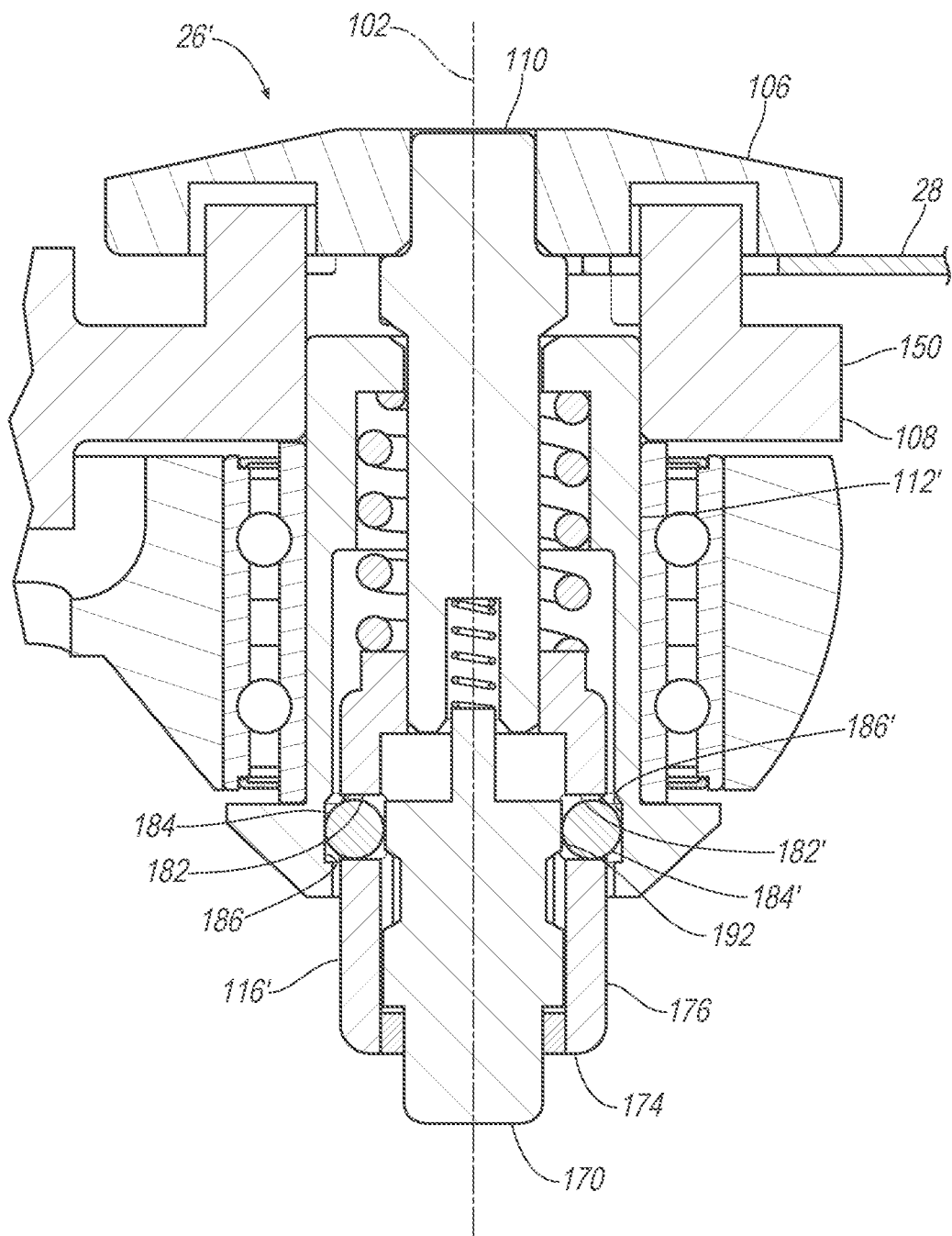
FIG. 25 is a sectional side view of the coupler of FIG. 15 holding an example blade with an example lock button in a locked position and the button and pin and cap in the retaining position.
Figure 26:
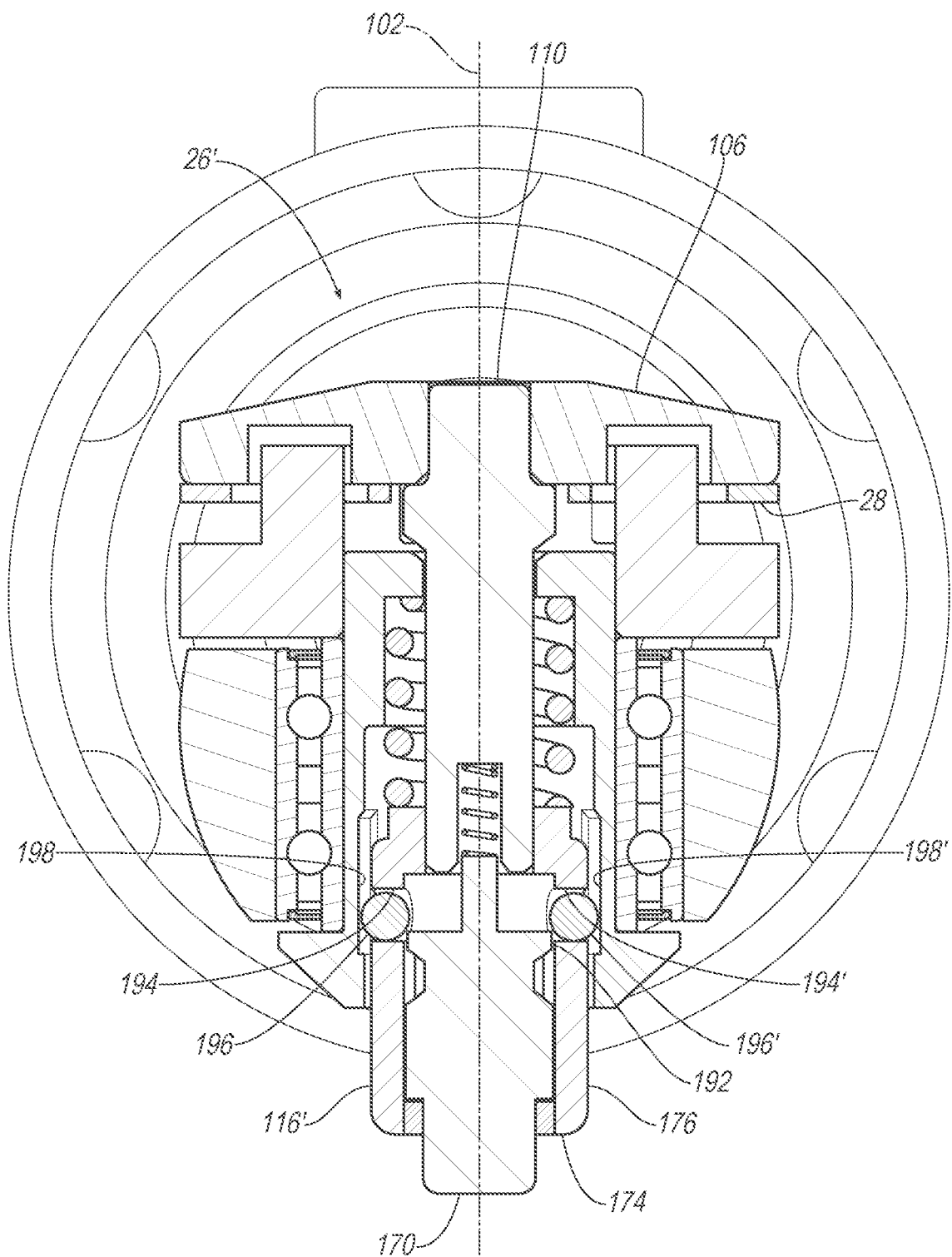
FIG. 26 is a sectional front view of the coupler of FIG. 15 holding the blade of FIG. 22 with the lock button in the locked position and the button and pin and cap in the retaining position.

FIGS. 25 and 26 show the release button 116' in the first retaining position and the lock button 170 in the first locked position.

FIGS. 25 and 26 provide sectional views of the coupler of FIG. 15 holding the example blade 28 with the lock button 170 in the first locked position and the example release button 116', pin 110, and cap 106 in the first retaining position. The lock button 170 extends beyond the first end 174 of the wall 176, indicating that the lock button 170 is in the one of the first and second locked positions. The first sliders 184, 184' are slidably disposed in their respective first slider apertures 182, 182'. The second sliders 196, 196' are slidably disposed in their respective second slider apertures 194, 194'. The first slider apertures 182, 182' are substantially aligned with the first cup receiving notches 186, 186' and with the upper portion of the outer surface 192 of the lock button 170. The first sliders 184, 184' are thus disposed in part in the first cup receiving notches 186, 186'. The second slider apertures 194, 194' are substantially aligned with the second cup receiving notches 198, 198' and with the upper portion of the outer surface 192 of the lock button. Accordingly, the second sliders 196, 196' are respectively disposed in part in the second cup receiving notches 198, 198'. The sliders 196, 196' are blocked from leaving the notches 198, 198' by engagement of the sliders 196, 196' against the upper part of the upper part of the outer surface 192 of the lock button 170. At the first retaining position of FIGS. 25 and 26, the second sliders 196 and 196' do not restrict upward axial movement of the cap 106 and the pin 110 due to the length of the second lock button receiving notches 200, 200'. Any effort to displace the cap 106 and pin 110 in any further in an upward direction is, however, resisted by engagement of the first sliders 184 and 184' against the respective ends of the notches 186, 186'. Such engagement resists any force against the cap 106 that might otherwise cause the cartridge 48 to become released from the coupler 26'.

Figure 27:
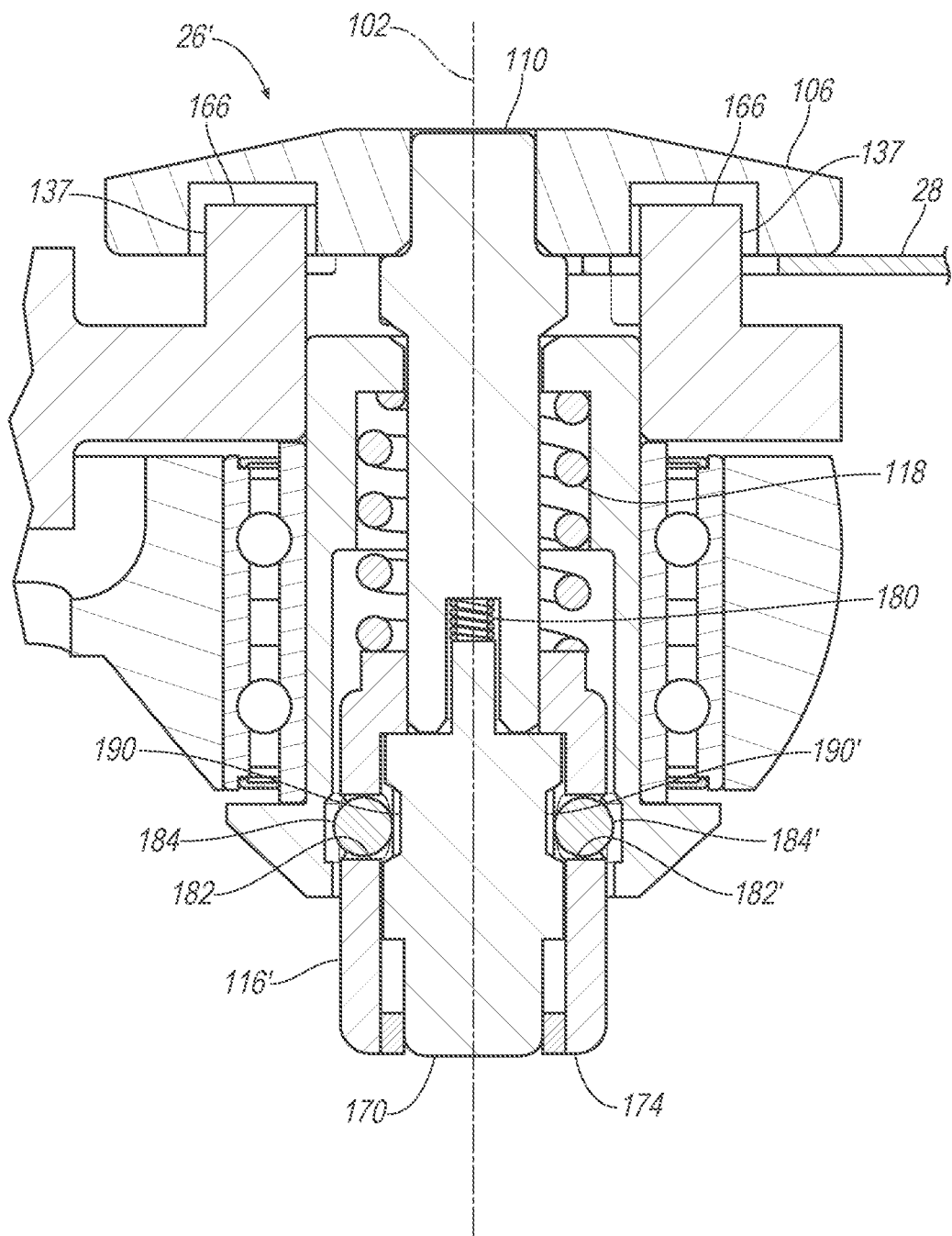
FIG. 27 is a sectional side view of the coupler of FIG. 15 holding the blade of FIG. 22 with the lock button in an unlocked position and the button and pin and cap in the retaining position.
Figure 28:
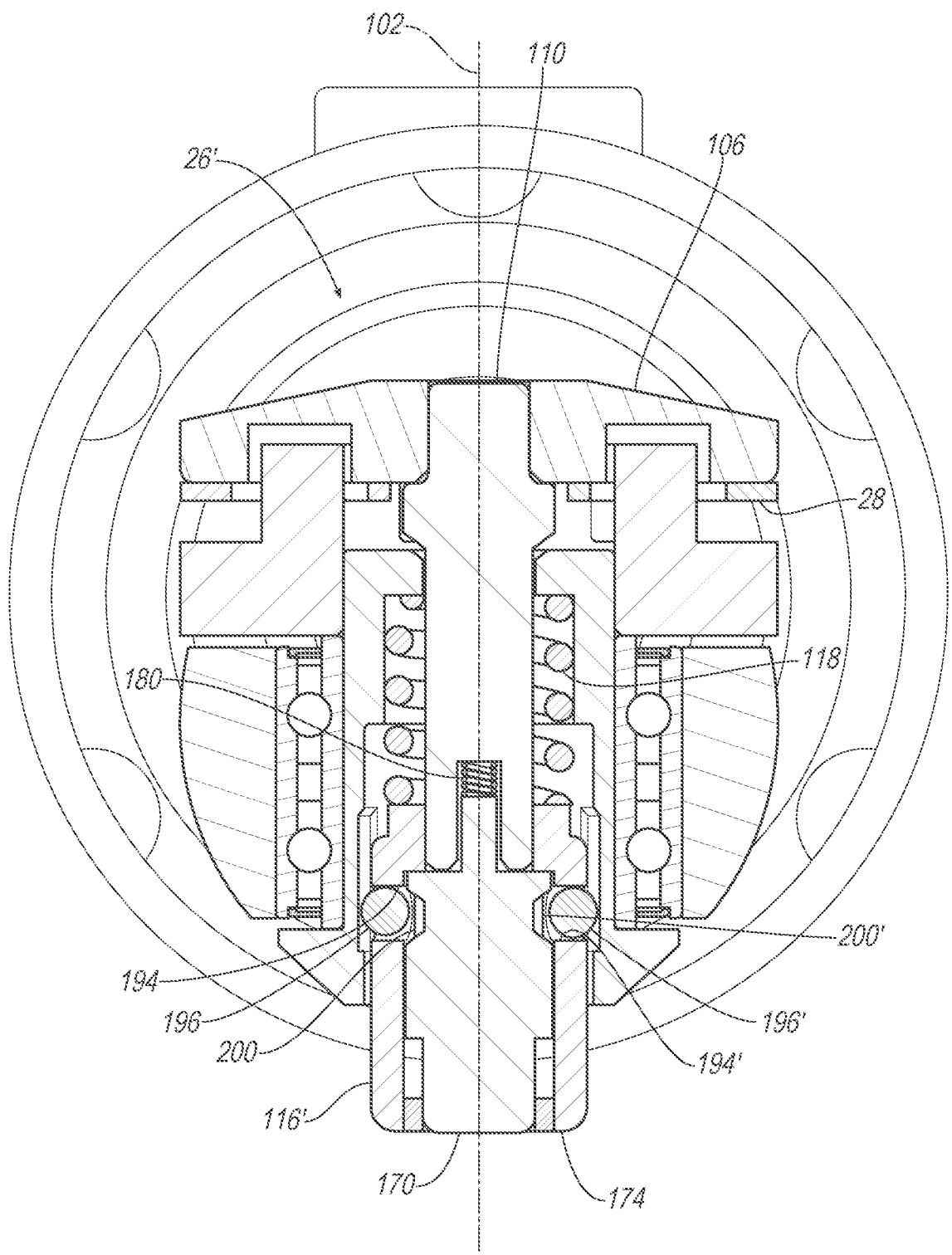
FIG. 28 is a sectional front view of the coupler of FIG. 15 holding the blade of FIG. 22 with the lock button in the unlocked position and the button and pin and cap in the retaining position.

FIGS. 27 and 28 show the coupler 26' and the blade 28' of FIGS. 25 and 26 in an unlocked and engaged condition, in which the lock button 170 is in the unlocked position and the release button 116' remains in the first retaining position with the blade 28 remaining below the ends of the prongs 137. The lock button 170 may be moved to the unlocked position by a user applying a force against the exposed end of the lock button 170 to overcome the force of the spring 180. The lock button 170 in the unlocked position may be substantially flush with the end 174 of the button wall 176, evidencing that it is in the unlocked position. With the lock button 170 in the unlocked position, the first lock button receiving notches 190, 190' are substantially aligned with the first slider apertures 182, 182', allowing the first sliders 184, 184' to move radially inwardly for receipt by the notches 190, 190'. Additionally, the second lock button receiving notches 200, 200' are substantially aligned with the second slider apertures 194, 194', allowing the sliders 196, 196' to move radially inwardly for receipt by the notches 200, 200'. The release button 116' may thus be moved, against the force of the coupler spring 118, to the second release position as illustrated in FIGS. 23 and 24. A first release position of the allowing removal of blades 28 may be substantially the same as the second release position. Cartridges 48 and blades 28 may be either removed from the coupler 26' or installed in the coupler 26' with the release button in the second release position. The position of the release button 116' and the associated position of the cap 106 that would allow removal of blades 28 may not require displacement of the release button 116' to the second release position. Each of the first release position and the second release position comprise points on a release range of travel of the assembled button 116', pin 110, and cap 106. The release position for a particular blade or cassette will depend at least in part on the thickness of the blade or cassette. The blade or cassette can still be either removed from or received by the coupler 26' when the associated release position is exceeded.

While not separately illustrated, the release of the blade 28 is essentially identical to the release of the cartridge 48 as illustrated in FIGS. 23 and 24. FIGS. 23 and 24 show the coupler 26' and the cartridge 48 of FIGS. 19 and 20 in an unlocked and released condition, in which the lock button 170 is in the unlocked position and the release button 116 has been moved upwardly against the force of the coupler spring 118 to the first release position which may be identical to the second release position. In the second first release position, as well as the first release position, the sliders are positioned as noted in the preceding paragraph. With the sliders 184, 184', 196, 196' so positioned, the release button 116' is able to travel upward, responsive to user input, until the upper engagement surface 143' of the release button 116' is against the step surface 142' of the cup 112'. With a corresponding displacement of the cap 106, the blade 28 may be lifted upwardly, with the blade 28 being able to clear the prongs 137, permitting removal of the blade 28 from the coupler 26'.

The coupler 26' may be beneficially used in the following ways. The coupler 26', without either a blade 28 or a cartridge 48 therein, appears as in the section views of FIG. 17, and 18. The handpiece 24 may be held by a user with one hand, a first hand. A digit, either a finger or a thumb, of the first hand may be used to press the lock button 170 upwardly from the first locked position of FIGS. 17 and 18 to the unlocked position of FIGS. 21, 22, 27, and 28.

The lock button 170 may be moved upwardly, against the force of spring 118, to the position described in the descriptions of FIGS. 21, 22, 27, and 28 and shown in those figures. That the lock button 170 may be fully displaced while the release button 116' is not substantially displaced may be achieved by selecting the lock spring 180 to have a significantly lower spring rate than a spring rate of the coupler spring 118. The resistance of the release button 116' to being depressed while the lock button is depressed may be additionally facilitated by having the coupler spring 118 compressed and thus preloaded in the closed position illustrated in FIGS. 17 and 18.

FIGS. 21, 22, 27, and 28 show a lower end of the lock button 170 as substantially flush with the first end 174 of the release button 116' in the unlocked position while the release button 116' remains in the engaged position. The flush position of the lower end of the lock button 170 may be sensed by the user, and recognized by the user as a signal that the lock button 170 is fully depressed and in the unlocked position. The position lock 168 may alternatively have the lock button 170 in its lock position extend below the first end 174 of the release button 116'. With such an arrangement, the signal benefit of the lock button 170 to the user may be reduced. However, the lock button 170 and the release button 116' would still operate effectively. The user may instead rely on an increase in the resistance of the buttons 170 and 116' to motion as the signal that the lock button 170 has reached the unlocked position and the release button 116' has been unlocked.

The user may continue to press against the lock button 170, in combination with the release button 116', displacing the assembled buttons 170, 116', pin 110, and cap 106 upward to the example position of FIGS. 23 and 24. While the upward travel of the assembled buttons 170, 116', pin 110, and cap 106 is illustrated as being limited by engagement of the upper engagement surface 143' against the step surface 142', the upward travel may be alternatively limited. One alternative mechanism for limiting travel of the assembled buttons 170, 116', pin 110, and cap 106 is to have the first end 174 be substantially flush with a lower end of the lower lip 130 when the assembled buttons 170, 116', pin 110, and cap 106 reach a maximum displacement. An outer diameter of the first end 174 may be selected to be smaller than a width of a typical adult finger. Travel of the assembled buttons 170, 116', pin 110, and cap 106 would thus not significantly exceed that achieved when first end 174 is flush with the lower end of the lip 130. With the coupler 26' in the resulting open position, either one of a cartridges 48 or a saw blade 28 may be placed within the coupler 26'.

The user may use a second hand to grip the body 34 of the cartridge saw blade 28', as between a finger and a thumb. The cartridge 48 may be positioned within the coupler 26' by vertically aligning the first outer side 64 with the bottom side 164 of the cap 106 and longitudinally aligning the cartridge 48 with the handpiece 24 and sliding the cartridge 48 proximally toward the handpiece 24 until, by way of example, the locating radial surface 44 engages the pin 110, or the second shell 58 contacts the raised section 160. The release button 116' may slowly be released while slightly laterally wiggling the cartridge to allow the prongs 137 to be aligned with and received by the apertures 40. As the button 116' is gradually lowered further, the cartridge may continue to be wiggled by the user to ensure engagement of the driving surfaces 36 against the prongs 137. The release button 116' is completely released by the user, and the lock button 170 is allowed to travel to the second locked position, responsive to the bias force applied by the lock spring 180. The release button 116' is now in the second retaining position and the lock button 170 is in the second locked position, as illustrated in FIGS. 19 and 20. With the release button 116' released, the spring 118 causes the bottom side 164 of the cap 106 to clamp the cassette 50 against the upper surface 154 of the drive locking portion 150.

With the cartridge 48 so retained, the saw system 20' may be used to cut material. The motor may be energized, causing the driver 108 to pivot about the axis 102 within the predetermined angular oscillation displacement range. The cassette 50 reduces blade whip, limiting a kerf thickness in the material being cut to substantially that of a thickness across the cutting teeth 46. As the saw blade 28' forms a kerf, and the blade 28' enters the kerf, a change in position of the saw may apply one of an axial force and a bending force, or a combination of the two, on the blade 28'. Either or both forces will result in a load against the bottom side 164 of the cap 106 in an upward direction. If not resisted, such force may cause the bottom side 164 of the cap 106, allowing the cartridge 48 to become loose and possibly separate from the coupler 26. Beneficially, the position lock 168 prevents such displacement of the cap 106. As illustrated in FIGS. 19 and 20, and particularly FIG. 20, the second sliders 196 and 196' engage the upper ends of notches 198 and 198' to resist upward displacement of the cap 106.

The cartridge 48 may be selectively released from the coupler 26' as illustrated in FIGS. 21-24, described above. The lock button 170 is moved by the user to the unlocked position shown in FIGS. 21 and 22. The release button 116' may then be moved to the release position shown in FIGS. 23 and 24. With the release button 116' held in the release position by the user, the user may withdraw the cartridge 48 from the coupler 26'. The user may need to press the first outer side 64 against the bottom side 164 of the cap 106 to ensure that the blade 28' clears the prongs 137.

The blade 28 may be similarly installed in the coupler 26' and retained therein. FIGS. 25 and 26 illustrate the coupler 26' with the blade 28 installed. With the release button 116' and lock button 170 both released by the user, the release button 116' is in the first retaining position and the lock button 170 is in the locked position. With the release button 116' released, the spring 118 causes the bottom side 164 of the cap 106 to clamp the proximal portion 30 of the blade 28 against the engaging surface 162 of the drive locking portion 150. As with the cartridge 48, there may be similar circumstances in the use of the saw system 20' in which the blade 28 applies a force against the cap 106 in a direction that could move the cap 106 away from the engaging surface 162, allowing undesired movement of the blade 28. Beneficially, the position lock 168 prevents such displacement of the cap 106. As illustrated in FIGS. 25 and 26, and particularly FIG. 25, the first sliders 184 and 184' engage the upper ends of notches 186 and 186' to resist upward displacement of the cap 106.

The blade 28 may be selectively released from the coupler 26' as illustrated in FIGS. 27-28, and FIGS. 23 and 24, described above. The lock button 170 is moved by the user to the unlocked position shown in FIGS. 27 and 28. The release button 116' may then be moved to the release position shown in FIGS. 24 and 25. With the release button 116' held in the release position by the user, the user may withdraw the blade 28 from the coupler 26'. The user may need to press the proximal portion 30 against the bottom side 164 of the cap 106 to ensure that the blade 28 clears the prongs 137.

Clauses directed to alternative configurations of the surgical saw blade and coupler described above:

I. A handpiece coupler (26) for engaging either of a surgical saw blade (28) and a surgical saw blade cartridge (48), the coupler comprising:
a housing head defining a pivot bore centered on an axis (38, 102);
a driver (108) axially fixed to the housing head and pivotable about the axis (38, 102) and defining a driver bore passing therethrough and substantially centered on the axis (38, 102) and the driver (108) including a blade engagement prong (137) on a first side of the driver radially spaced from the axis;
a cup (112) fixed to the driver (108) for unitary movement therewith and having an inside wall surface substantially centered on the axis (38, 102) and axially extending from a second side of the driver into the pivot bore;
a pin (110) slidably disposed in the driver bore and the cup (112) for selective axial displacement therein and relative thereto;
a cap (106) fixed to a first end of the pin (110) and the cap extending radially beyond the prong (137);
a release button (116) fixed to a second end of the pin (110) for selective engagement by a user and defining a lock cavity (172) therein and the lock cavity (172) and an outer surface of the release button (116) defining a button wall (176) therebetween;
a coupler spring (118) disposed between the driver (108) and the pin (110) biasing the pin (110) toward a closed position; and
a lock button (170) slidably disposed in the lock cavity (172) and having two locked positions and an unlocked position therein.

II. The handpiece coupler of clause I, wherein the lock button comprises part of a position lock further comprising a lock spring disposed between the lock button and the pin and the lock spring biasing the lock button toward the locked positions.

III. The handpiece coupler of clause II, wherein the lock button comprises part of the position lock further comprising:
a first slider (184); and
a second slider (196),
wherein:
the release button (116) has formed therein:
 an open first end of the cavity,
 a first slider aperture (182) in slidable receipt of the first slider (184) and passing through the button wall at a first axial and circumferential location, and
 a second slider aperture (194) in slidable receipt of the second slider (196) and passing through the button wall in a second axial location offset from the first axial location and a second circumferential location offset from the first circumferential location.

IV. The handpiece coupler of clause III, wherein the lock button extends beyond a first end of the button wall in the locked positions and is substantially flush with the first end of the button wall in the unlocked position.

V. The handpiece coupler of either of clauses III or IV, wherein the position lock further comprises a plurality of notches in the inside wall surface of the cup and an outer surface of the lock button for selective engagement by the sliders.

VI. The handpiece coupler of clause V, the plurality of notches including:
a first lock button receiving notch (190) in the outer surface of the lock button;
a first cup receiving notch (186) in the inside wall surface of the cup;
a second cup receiving notch (198) in the inside wall surface of the cup; and
a second lock button receiving notch (200) in the outer surface of the lock button.

VII. The handpiece coupler of clause VI, wherein:
the first slider (184) is disposed:
 at least in part in the first slider aperture (182) for axial movement with the release button in all positions of the release button and the lock button,
 in part in the first cup receiving notch (186) with the release button in a first retaining position and the lock button in a first locked position,
 in part in the first lock button receiving notch (190) with the release button in the first retaining position through a first release position and the lock button in the unlocked position,
 in part in the first lock button receiving notch with the release button in a second retaining position and the lock button in a second locked position, and
 in part in the first lock button receiving notch with the release button in the second retaining position through a second release position and the lock button in the unlocked position; and
the second slider is disposed:
 at least in part in the second slider aperture (194) for axial movement with the release button in all positions of the release button and the lock button,
 in part in the second cup receiving notch (198) with the release button in the first retaining position and the lock button in the first locked position,
 in part in the second lock button receiving notch (200) with the release button in the first retaining position through the first release position of the release button and the lock button in the unlocked position,
 in part in the second cup receiving notch with the release button in the second retaining position and the lock button in the second locked position, and in part in the second lock button receiving notch with the release button in the second retaining position through the second release position of the release button and the lock button in the unlocked position.

VIII. The handpiece coupler of clause VII, wherein:
the first retaining position is achieved when a blade without a damper cassette is received by the coupler; and
the second retaining position is achieved when a blade cartridge including the damper cassette is received by the coupler.

IX. The handpiece coupler of clause III, wherein the lock button comprises part of the position lock further comprising:
a twin first slider (184'); and
a twin second slider (196'),
wherein:
the release button (116) has formed therein:
 a twin first slider aperture in slidable receipt of the twin first slider and passing through the button wall, and
 a twin second slider aperture in slidable receipt of the twin second slider and passing through the button wall.

X. The handpiece coupler of clause VIII, wherein the position lock further comprises a plurality of notches in the inside wall surface of the cup and an outer surface of the lock button for selective engagement by the sliders.

XI. The handpiece coupler of clause IX, the plurality of notches including:
a first lock button receiving notch and a mirror image first lock button receiving notch in the outer surface of the lock button;
a first cup receiving notch and a mirror image first cup receiving notch in the inside wall surface of the cup;
a second cup receiving notch and a mirror image second cup receiving notch in the inside wall surface of the cup; and
a second lock button receiving notch and a mirror image second lock button receiving notch in the outer surface of the lock button.

XII. The handpiece coupler of clause X, wherein:
the first slider is disposed:
 at least in part in the first slider aperture for axial movement with the release button in all positions of the release button and the lock button,
 in part in the first cup receiving notch with the release button in a first retaining position and the lock button in a first locked position, in part in the first lock button receiving notch with the release button in the first retaining position through a first release position and the lock button in the unlocked position,
in part in the first lock button receiving notch with the release button in a second retaining position and the lock button in a second locked position, and
in part in the first lock button receiving notch with the release button in the second retaining position through a second release position and the lock button in the unlocked position;
the first twin slider is disposed:
at least in part in the twin first slider aperture for axial movement with the release button in all positions of the release button and the lock button,
in part in the mirror image first cup receiving notch with the release button in a first retaining position and the lock button in the first locked position,
in part in the mirror image first lock button receiving notch with the release button in the first retaining position through the first release position and the lock button in the unlocked position,
in part in the mirror image first lock button and the lock button in the second locked position, and
in part in the mirror image first lock button receiving notch with the release button in the second retaining position through the second release position and the lock button in the unlocked position;
the second slider is disposed:
at least in part in the second slider aperture for axial movement with the release button in all positions of the release button and the lock button,
in part in the second cup receiving notch with the release button in the first retaining position and the lock button in the first locked position,
in part in the second lock button receiving notch with the release button in the first retaining position through the first release position of the release button and the lock button in the unlocked position,
in part in the second cup receiving notch with the release button in the second retaining position and the lock button in the second locked position, and
in part in the second lock button receiving notch with the release button in the second retaining position through the second release position of the release button and the lock button in the unlocked position; and
the twin second slider is disposed:
at least in part in the twin second slider aperture for axial movement with the release button in all positions of the release button and the lock button,
in part in the mirror image second cup receiving notch with the release button in the first retaining position and the lock button in the first locked position,
in part in the mirror image second lock button receiving notch with the release button in the first retaining position through the first release position of the release button and the lock button in the unlocked position,
in part in the mirror image second cup receiving notch with the release button in the second retaining position and the lock button in the second locked position, and
in part in the mirror image second lock button receiving notch with the release button in the second retaining position through the second release position of the release button and the lock button in the unlocked position.

XIII. The handpiece coupler of clause XI, wherein:
the first retaining position is achieved when a blade without a damper cassette is received by the coupler; and
the second retaining position is achieved when a blade cartridge including the damper cassette is received by the coupler.

XIV. The handpiece coupler of any of clauses III through XIII, wherein the sliders are substantially rigid spheres.

XV. The handpiece coupler of any one of clauses I through XIV, wherein a first locked position is configured to secure the cap in a first retaining position spacing the cap a first distance from the driver; and
wherein a second locked position is configured to secure the cap in a second retaining position spacing the cap a second distance from the driver In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A saw blade cartridge configured to be removably mounted to a coupler of a powered surgical saw, the cartridge comprising:
a saw blade including:
a proximal portion including a driving surface and a mount axis,
a distal portion including cutting teeth, and
a blade body between the distal and proximal portions; and
a cassette disposed over the proximal portion and configured to be releasably received by the coupler of the powered surgical saw, the cassette including:
first and second cassette portions opposed across the proximal portion, each cassette portion comprising:
a shell having an outer side and an opposed inner side with an associated inner edge and a first stiffness, and
a damper of a second stiffness less than the first stiffness and disposed on an inner side of the shell; and
wherein the shell of each of the first and second cassette portions is formed of a first material and the dampers are formed of a second material, wherein the second material is elastomeric.

2. The saw blade cartridge of claim 1, wherein the cassette portions are in alignment with each other and fixed relative to the proximal portion and the shells are fixed to each other with the dampers contacting the proximal portion.

3. The saw blade cartridge of claim 1, wherein the inner side of the shell of each of the first and second cassette portions defines a receiving pocket for the respective damper and each pocket is in receipt of the corresponding damper.

4. The saw blade cartridge of claim 1, wherein each damper extends beyond the inner edge of the respective shell.

5. The saw blade cartridge of claim 1, wherein the cassette does not entirely overlap the driving surface.

6. The saw blade cartridge of claim 1, wherein:
the proximal portion of the saw blade has a first thickness and is planar and the blade body is planar and has a second thickness.

7. The saw blade cartridge of claim 6, wherein:
the outer sides of the first and second cassette portions are planar and the cartridge has a uniform third thickness across the outer sides.

8. The saw blade cartridge of claim 1, wherein the shell of at least one of the first and second cassette portions includes a connecting tab extending beyond the associated inner edge.

9. The saw blade cartridge of claim 8, wherein the connecting tab is disposed in a connecting opening in the saw blade, and wherein the connecting tab is fixed to the shell of the opposed cassette portion.

10. A saw blade cartridge configured to be removably mounted to a coupler of a powered surgical saw, the cartridge comprising:
a saw blade including:
a proximal portion including a driving surface and a mount axis,
a distal portion including cutting teeth, and
a blade body between the distal and proximal portions; and
a cassette disposed over the proximal portion and including:
first and second cassette portions opposed across the proximal portion, each cassette portion comprising:
a shell having an outer side and an opposed inner side with an associated inner edge and a first stiffness, and
a damper of a second stiffness less than the first stiffness and disposed on an inner side of the shell;
wherein the shell of at least one of the first and second cassette portions includes a connecting tab extending beyond the associated inner edge and configured to couple the first and second cassette portions to one another.

11. The saw blade cartridge of claim 10, wherein the connecting tab is disposed in a connecting opening in the saw blade, and wherein the connecting tab is fixed to the shell of the opposed cassette portion.

12. The saw blade cartridge of claim 10, wherein the cassette portions are in alignment with each other and fixed relative to the proximal portion and the shells are fixed to each other with the dampers contacting the proximal portion.

13. The saw blade cartridge of claim 10, wherein the shell of each of the first and second cassette portions are formed of a first material and the dampers are formed of a second material, wherein the second material is elastomeric.

14. The saw blade cartridge of claim 13, wherein the inner side of the shell of each of the first and second cassette portions defines a receiving pocket for the respective damper and each pocket is in receipt of the corresponding damper.

15. The saw blade cartridge of claim 13, wherein each damper extends beyond the inner edge of the respective shell.

16. The saw blade cartridge of claim 10, wherein the cassette does not entirely overlap the driving surface.

17. The saw blade cartridge of claim 10, wherein:
the proximal portion of the saw blade has a first thickness and is planar and the blade body is planar and has a second thickness.

18. The saw blade cartridge of claim 17, wherein:
the outer sides of the first and second cassette portions are planar and the cartridge has a uniform third thickness across the outer sides.

* * * * *